US007741019B2

(12) United States Patent
Diamandis et al.

(10) Patent No.: US 7,741,019 B2
(45) Date of Patent: Jun. 22, 2010

(54) DETECTION OF OVARIAN CANCER

(75) Inventors: Eleftherios P. Diamandis, Toronto (CA); Liu-Ying Luo, Toronto (CA)

(73) Assignee: Mount Sinai Hospital, Toronto, Ontario (CA)

( * ) Notice: Subject to any disclaimer, the term of this patent is extended or adjusted under 35 U.S.C. 154(b) by 493 days.

(21) Appl. No.: 10/415,222

(22) PCT Filed: Nov. 1, 2001

(86) PCT No.: PCT/CA01/01543

§ 371 (c)(1),
(2), (4) Date: Nov. 5, 2003

(87) PCT Pub. No.: WO02/37112

PCT Pub. Date: May 10, 2002

(65) Prior Publication Data

US 2004/0115745 A1     Jun. 17, 2004

Related U.S. Application Data

(60) Provisional application No. 60/244,837, filed on Nov. 1, 2000.

(51) Int. Cl.
*C12Q 1/00*        (2006.01)
*G01N 33/574*    (2006.01)
(52) U.S. Cl. ........................................ 435/4; 435/7.23
(58) Field of Classification Search ...................... None
See application file for complete search history.

(56) References Cited

U.S. PATENT DOCUMENTS

| 4,921,790 | A | * | 5/1990 | O'Brien | ...................... 435/7.94 |
| 5,736,377 | A | | 4/1998 | Band | |
| 5,843,694 | A | * | 12/1998 | Band | ........................... 435/23 |
| 6,962,793 | B2 | | 11/2005 | Diamandis | |
| 7,022,497 | B1 | | 4/2006 | Yousef et al. | |
| 7,504,214 | B2 | | 3/2009 | Erlander et al. | |
| 2003/0108963 | A1 | | 6/2003 | Schlegel et al. | |
| 2004/0058342 | A1 | | 3/2004 | Diamandis | |
| 2004/0096915 | A1 | | 5/2004 | Diamandis | |
| 2004/0203012 | A1 | | 10/2004 | Diamandis | |
| 2005/0106586 | A1 | | 5/2005 | Diamandis | |
| 2005/0176002 | A1 | | 8/2005 | Diamandis | |
| 2005/0287528 | A1 | | 12/2005 | Diamandis | |
| 2006/0073525 | A1 | | 4/2006 | Yousef | |
| 2006/0078941 | A1 | | 4/2006 | Santin | |
| 2006/0134114 | A1 | | 6/2006 | Yousef | |
| 2006/0134120 | A1 | | 6/2006 | Diamandis | |
| 2006/0141471 | A1 | | 6/2006 | Diamandis | |
| 2006/0159616 | A1 | | 7/2006 | Diamandis | |
| 2006/0223059 | A1 | | 10/2006 | Yousef | |
| 2006/0269971 | A1 | | 11/2006 | Diamandis | |
| 2007/0212721 | A1 | * | 9/2007 | Fischer et al. | .................. 435/6 |

FOREIGN PATENT DOCUMENTS

| WO | 98/20117 | 5/1998 |
| WO | WO-00/53776 | 9/2000 |
| WO | WO-02/14485 | 2/2002 |
| WO | WO-02/35232 | 5/2002 |
| WO | WO-02/37112 | 5/2002 |
| WO | WO-02/097438 | 12/2002 |
| WO | WO-03/033731 | 4/2003 |
| WO | WO 2005/118840 | 12/2005 |

OTHER PUBLICATIONS

Berek et al, "Ovarian Cancer Screening: The Use of Serial Complementary Tumor Markers to Improve Sensitivity and Specificity for early Detection", Cancer (1995); 76:2092-2096.*
Bjartell et al, The Histochemical Journal 1999, vol. 31, p. 45-52.*
Badgwell et al, Disease Markers, 2007, vol. 23, No. 5-6, pp. 397-410, abstract only.*
Zhang et al., Gynecologic Oncology, 2007, vol. 107, pp. 526-531.*
Visintin et al., Clinical Cancer Research, 2008, vol. 14, No. 4, pp. 1065-1072.*
Badgwell et al., "Early Detection of Ovarian Cancer", Disease Markers, 2007, vol. 23, No. 5-6, pp. 397-410.*
Aznavoorian et al., "Molecular Aspects of Tumor Cell Invasion and Metastasis", Cancer (1993); 71: 1368-1383.
Berek et al., "Ovarian Cancer Screening: The Use of Serial Complementary Tumor Markers To Improve Sensitivity and Specificity for Early Detection", Cancer (1995); 76: 2092-2096.
Bhoola et al., "Bioregulation of Kinins: Kallikreins, Kininogens, and Kininases", Pharmacological Reviews (1992); 44: 1-80.
Burger et al., "Inhibin and ovarian cancer", Journal of Reproductive Immunology (1998); 39: 77-87.
Chu, "Prostate-Specific Antigen and Early Detection of Prostate Cancer", Tumor Biology (1997); 18: 123-134.
Clements, "The Molecular Biology of the Kallikreins and their Roles in Inflammation", In: Farmer SG (ed) The Kinin System, Academic Press (1997); 5: 71-97.
Daidone et al., "Laminin Receptors, Collagenase IV and Prognosis in Node-Negative Breast Cancers", International Journal of Cancer (1991); 48: 529-532.
Diamandis et al., "The New Human Kallikrein Gene Family: Implications in Cacinogenesis", Trends in Endocrinology and Metabolism (2000); 11: 54-60.
Duffy et al., "Urokinase-Plasminogen Activator, a New and Independent Prognostic Marker in Breast Cancer", Cancer Research (1990); 50: 6827-6829.

(Continued)

*Primary Examiner*—Jon P Weber
*Assistant Examiner*—Laura Schuberg
(74) *Attorney, Agent, or Firm*—Howson & Howson LLP

(57) ABSTRACT

A method for the diagnosis, prognosis, and monitoring of ovarian cancer in a subject by detecting hK10 in a sample from the subject, preferably a serum sample or tumor tissue extract. hK10 may be measured using a reagent that detects or binds to hK10 preferably antibodies specifically reactive with hK10 or a part thereof. Imaging methods for tumors associated with hK10 are also described using an agent that binds to hK10 which had a label for imaging the tumor.

17 Claims, 18 Drawing Sheets

OTHER PUBLICATIONS

Duffy, " The role of Proteolytic enzymes in cancer invasion and metastasis", Clinical and Experimental Metastasis (1992); 10: 145-155.

Foekens et al., "Prognostic Value of Urokinase-type Plasminogen Activator in 671 Primary Breast Cancer Patients", Cancer Research (1992); 52: 6101-6105.

Goyal et al., "The Role for NES1 Serine Protease as a Novel Tumor Suppressor", Cancer Research (1998); 58: 4782-4786.

Lambert-Messerlian, "Is inhibin a serum marker for ovarian cancer?", European Journal of Endocrinology (2000); 142:331-333.

Liu et al., "Identification of a Novel Serine Protease-like Gene, the Expression of Which Is Down-Regulated during Breast Cancer Progression", Cancer Research (1996); 56: 3371-3379.

Luo et al., "Structural Characterization and Mapping of the Normal Epithelial Cell-Specific 1 Gene", Biochemical and Biophysical Research Communications (1998); 247: 580-586.

McCormack et al., "Molecular Forms of Prostate-Specific Antigen and the Human Kallikrein Gene Family: A New Era", Urology (1995); 45: 729-744.

Pisani et al., "Estimates of the Worldwide Mortality From Eighteen Major Cancers in 1985. Implications for Prevention and Projections of Future Burden", International Journal of Cancer (1993); 55: 891-903.

Riegman et al., "Characterization of the Human Kallikrein Locus", Genomics (1992); 14: 6-11.

Riman et al., "Hormonal aspects of epithelial ovarian cancer: review of epidemiological evidence", Clinical Endocrinology (1998); 49: 695-707.

Rittenhouse et al., "Human Kallikrein 2 (hK2) and Prostate-Specific Antigen (PSA): Two Closely Related, But Distinct, Kallikreins in the Prostate", Critical Reviews in Clinical Laboratory Sciences (1998); 35: 275-368.

Stenman, "New Ultrasensitive Assays Facilitate Studies on the Role of Human Glandular Kallikrein (hK2) as a Marker for Prostatic Disease", Clinical Chemistry (1999); 45: 753-754.

Thorpe et al., "Association between High Concentrations of $M_r$ 52,000 Cathepsin D and Poor Prognosis in Primary Human Breast Cancer", Cancer Research (1989); 49: 6008-6014.

Xu et al., "OVX1 Radioimmunoassay Complements CA-125 for Predicting the Presence of Residual Ovarian Carcinoma at Second-Look Surgical Surveillance Procedures", Journal of Clinical Oncology (1993); 11: 1506-1510.

Luc et al., "The Normal Epithelial Cell-Specific 1 (NES1) Gene is Up-Regulated by Steroid Hormones in the Breast Carcinoma Cell Line BT-474", Anticancer Research (2000); 20: 981-986.

Luo et al., "Expression of the normal epithelial cell-specific 1 (*NES1*; KLK 10) candidate tumour suppressor gene in normal and malignant testicular tissue", British Journal of Cancer (2001); 85(2): 220-224.

Bharaj et al., "Identification of Single Nucleotide Polymorphisms in the Human Kallikrein 10 (KLK10) Gene and Their Association with Prostate, Breast, Testicular and Ovarian Cancers" The Prostate, 51:35-41 (Apr. 1, 2002).

Dhar et al, "Analysis of Normal Epithelial cell Specific-1 (NEW1)/ Kallikrein 10 mRNA Expression by in Situ Hybridization, a Novel Marker for Breast Cancer", Clin. Cancer Res., 7:3393-3398 (Nov. 2001).

Luo et al, "Higher expression of human kallikrein 10 in breast cancer tissue predicts tamoxifen resistance", Brit. J. Cancer, 86(11):1790-1796 (Jun. 5, 2002).

Petraki et al, "Immunohistochemical localization of human kallikreins 6, 10 and 13 in benign and malignant prostatic tissues", Prostate Cancer and Prostatic Dis., 6:223-227 (2003).

Luo et al, "Prognostic Value of Human Kallikrein 10 Expression in Epithelial Ovarian Carcinoma", Clin. Cancer Res., 7:2372-2379 (Aug. 2001).

Luo et al, "Human Kallikrein 10: A novel tumor marker for ovarian carcinoma?", Clin. Chim. Acta 306:111-118 (Apr. 2001).

Sidiropoulos, M., et al., Downregulation of Human Kallikrein 10 (KLK10/NES1) by CpG Island Hypermethylation in Breast, Ovarian and Prostate Cancers, Tumor Biology, vol. 26, (Oct. 26, 2005), pp. 324-336.

Santin, A, et al., Overexpression of Kallikrein 10 (hK10) in Uterine Serous Papillary Carcinomas, American J. Obstetrics and Gynecology, vol. 194, (Oct. 2005), pp. 1269-1302.

Ruckert, F., et al., Co-expression of KLK6 and KLK10 as Prognostic Factors for Survival in Pancreatic Ductal Adenocarcinoma, British J. of Cancer, vol. 99, (Oct. 14, 2008), pp. 1484-1492.

Yousef, G., et al., Identification of New Splice Variants and Differential Expression of the Human Kallikrein 10 Gene, a Candidate Cancer Biomarker, Tumor Biology, vol. 26, (Aug. 9, 2005), pp. 227-235.

K. Oikonomopoulou et al., "Kallikreins as Markers of Disseminated Tumour Cells in Ovarian Cancer-A Pilot Study", Tumor Biology, 27:104-114 (Mar. 24, 2006).

D. G. Rosen et al, "Potential Markers That Complement Expression of CA125 in Epithelial Ovarian Cancer", Gynecologic Oncology 99:267-277 (Aug. 2, 2005).

I-M Shin et al, "Ovarian Cancer Specific Kallikrein Profile in Effusions", Gynecologic Oncology, 105:501-507 (Feb. 15, 2007).

H. S. Shvartsman et al, "Overexpression of Kallikrein 10 in Epithelial Ovarian Carcinomas", Gynecologicl Oncology, 90:44-50 (May 20, 2003).

Y. Zhang et al, Human Kallikrein 10, a Predictive Marker for Breast Cancer, Biological Chemistry, 387:715-721 (Jun. 2006).

\* cited by examiner

DETECTION OF OVARIAN CANCER

FIELD OF THE INVENTION

The invention relates to diagnostic, prognostic, and monitoring methods for ovarian cancer.

BACKGROUND OF THE INVENTION

The human kallikrein gene family is a group of genes that are clustered on chromosome 19q13.3-q13.4 and share significant homologies at both the nucleotide and amino acid levels (1-5). Until recently, this family was thought to contain only three genes, including KLK1 (encoding for human kallikrein 1, hK1; also known as pancreaticrenal kallikrein), KLK2 (encoding for human kallikrein 2, hK2) and KLK3 (encoding for human kallikrein 3, hK3; also known as prostate-specific antigen, PSA). Over the last 2-3 years, new genes were identified in the same chromosomal region and are now considered to be members of the kallikrein gene family (6). These new kallikrein genes are currently known with various empirical names. An international group of investigators has recently agreed on new human kallikrein gene nomenclature (7). This gene family now contains at least 15 genes which are designated KLK1 . . . KLK15, while their encoded proteins are designated as hK1 . . . hK15.

The normal epithelial cell-specific 1 (NES1) gene is one of these newly identified genes. With the new nomenclature, NES1 is designated as KLK10 and the encoded protein as hK10. KLK10 was isolated with subtractive hybridization, between radiation-transformed and non-transformed breast epithelial cells (8). KLK10 resides on chromosome 19q13.4, spans about 5.5 kb of genomic DNA sequence and contains six exons (one untranslated) and five introns (9). hK10 is a secreted serine protease and its amino acid sequence has 35-40% identity and 50-55% similarity with other members of the human kallikrein gene fly, including PSA. The physiological function of hK10 has not as yet been elucidated. Since the KLK10 gene is down-regulated in breast cancer cell lines, it is considered to play a role in the regulation of normal cell growth. Goyal et al. have recently suggested that KLK10 may encode for a tumor suppressor gene (10). When the KLK10 gene was transfected into the tumorigenic breast cancer cell line MDA-MB-231, its anchorage-independent growth was reduced and when this cell line was inoculated into nude mice, tumor formation was significantly decreased.

Ovarian cancer is a serious disease which causes more deaths than any other cancer of the female reproductive system (13). Since survival could be dramatically improved if the disease is diagnosed early (14), there is great interest in the identification of biomarkers that could aid in the early detection and facilitate grading and/or staging (15). Unfortunately, the current serological markers for ovarian carcinoma, including CA125 (16-19), inhibin (20-23), OVX1 (24) as well as many other markers (reviewed in 25) have shown some promise but have not gained wide clinical acceptance. Another potential ovarian cancer marker, lysophosphatidicacid appears to also have some value for this purpose (26).

There is an urgent need for discovery and validation of new serum biomarkers for ovarian carcinoma. Early diagnosis of ovarian cancer with serological analysis may improve clinical outcomes through administration of effective treatment.

SUMMARY OF THE INVENTION

A highly sensitive hK10 immunoassay for the measurement of hK10 in various biological fluids was developed (Example 1). Using this sensitive assay the hK10 concentration in serum was found to be significantly increased in a large proportion of patients with ovarian cancer. hK10 was also measured in ovarian cancer cytosolic extracts and found to be elevated in comparison with normal and benign ovarian tissues. The elevated levels were more strongly associated with late disease stages serious histological type, suboptimal debulking, and large residual tumor.

Thus, hK10 constitutes a new biomarker for prognosis, diagnosis and monitoring of ovarian cancer. hK10 may be used to diagnose and monitor late stage ovarian cancer, it may be used as a biomarker before surgery or after relapse.

hK10, and agents that bind to hK10 may be used to detect ovarian cancer and in particular they can be used in the diagnostic evaluation of ovarian cancer, and the identification of subjects with a predisposition to such disorders.

The present invention relates to a method for diagnosing and monitoring ovarian carcinoma in a subject comprising measuring hK10 in a sample from the subject hK10 may be measured using a reagent that detects hK10 preferably antibodies specifically reactive with hK10 or a part thereof.

In an aspect of the invention, a method is provided for detecting hK10 associated with ovarian cancer in a patient comprising:

(a) taking a sample derived from a patient;

(b) detecting or identifying in the sample hK10; and (c) comparing the detected amount with an amount detected for a standard.

The invention also relates to a method of screening a subject for ovarian cancer comprising: (a) obtaining a biological sample from a subject; (b) detecting the amount of hK10 in said sample; and (c) comparing said amount of hK10 detected to a predetermined standard, where detection of a level of hK10 greater than that of a standard indicates the presence of ovarian cancer, in particular late stage ovarian cancer.

The terms "detecting" or "detect" include assaying, imaging or otherwise establishing the presence or absence of the target hK10, subunits thereof, or combinations of reagent bound targets, and the like, or assaying for, imaging, ascertaining, establishing, or otherwise determining one or more factual characteristics of ovarian cancer, metastasis, stage, or similar conditions. The term encompasses diagnostic, prognostic, and monitoring applications for hK6.

In an embodiment, the invention relates to a method for detecting ovarian cancer in a subject by quantitating hK10 in a biological sample from the subject comprising (a) reacting the biological sample with an antibody specific for hK10 which is directly or indirectly labelled with a detectable substance; and (b) detecting the detectable substance.

In an embodiment, the invention relates to a method for diagnosing and monitoring ovarian carcinoma in a subject by quantitating hK10 in a biological sample from the subject comprising (a) reacting the biological sample with an antibody specific for hK10 which is directly or indirectly labelled with a delectable substance; and (b) detecting the detectable.

Embodiments of the methods of the invention involve (a) reacting a biological sample from a subject with an antibody specific for hK10 which is directly or indirectly labelled with an enzyme; (b) adding a substrate for the enzyme wherein the substrate is selected so that the substrate, or a reaction product of the enzyme and substrate, forms fluorescent complexes; (c) quantitating hK10 in the sample by measuring fluorescence of the fluorescent complexes; and (d) comparing the quantitated levels to that of a standard.

A preferred embodiment of the invention comprises the following steps (a) incubating a biological sample with a first antibody specific for hK10 which is directly or indirectly labeled with a detectable substance, and a second antibody specific for hK10 which is immobilized;

(b) separating the first antibody from the second antibody to provide a first antibody phase and a second antibody phase;

(c) detecting the detectable substance in the first or second antibody phase thereby quantitating hK10 in the biological sample; and (d) comparing the quantitated hK10 with a standard.

A standard used in a method of the invention may correspond to hK10 levels obtained for samples from healthy control subjects, from subjects with benign die subjects with early stage disease, or from other samples of the subject. Increased levels of hK10 as compared to the standard may be indicative of ovarian cancer, in particular late stage ovarian cancer.

The invention also contemplates the methods described herein using multiple markers for ovarian cancer. Therefore, the invention contemplates a method for analyzing a biological sample for the presence of hK10 and other markers that are specific indicators of ovarian cancer. Other markers include markers to kallikreins such as human stratum corneum chymotryptic enzyme (HSCCE), kallikrein 4, kallikrein 5, kallikrein 6, kallikrein 8, kallikrein 9, CA125, CA15-3, CA19-9, OVX1, lysophosphatidic acid (LPA) and carcinoembryonic antigen (CEA). Preferably the other mar are markers to kallikreins. In a preferred embodiment, the markers are two or more of hK6 and CA 125. The methods described herein may be modified by including reagents to detect the additional markers, or nucleic acids for the markers.

The invention also relates to a method for imaging a tumor associated with hK10 comprising (a) incubating the tumor with an agent that binds to hK10 for a sufficient period of time to permit the agent to bind to hK10 associated with the tumor, where the agent carries a label for imaging the tumor;

(b) detecting the presence of the label localized to the tumor.

The invention contemplates an in vivo method comprising administering to a mammal one or more agent that carries a label for imaging and binds to a kallikrein, preferably hK10, and then imaging the mammal.

According to a preferred aspect of the invention, an in vivo method for imaging ovarian cancer is provided comprising:

(a) injecting a patient with an agent that binds to kallikrein 10, the agent carrying a label for imaging ovarian cancer;

(b) allowing the agent to incubate in vivo and bind to kallikrein 10 associated with the ovarian cancer; and (c) detecting the presence of the label localized to the ovarian cancer.

In an embodiment of the invention the agent is an antibody which recognizes the kallikrein. In another embodiment of the invention the agent is a chemical entity which recognizes the kallikrein.

The agent carries a label to image the kallikreins. Examples of labels useful for imaging are radiolabels, fluorescent labels (e.g fluorescein and rhodamine), nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes can also be employed The invention also contemplates the localization or imaging methods described herein using multiple markers for ovarian cancer. For example, a method for imaging ovarian cancer may further comprise injecting the patient with one or more of an agent that binds to human stratum corneum chymotryptic enzyme (HSCCE), kallikrein 4, kallikrein 5, kallikrein 6, kallikrein 8, kallikrein 9, CA125, CA15-3, CA19-9, OVX1, lysophosphatidic acid (LPA) or carcinoembryonic antigen (CEA), preferably CA 125.

The invention also relates to kits for carrying out the methods of the invention.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will now be described in relation to the drawings in which.

DETAILED DESCRIPTION OF THE INVENTION

Figure 1:
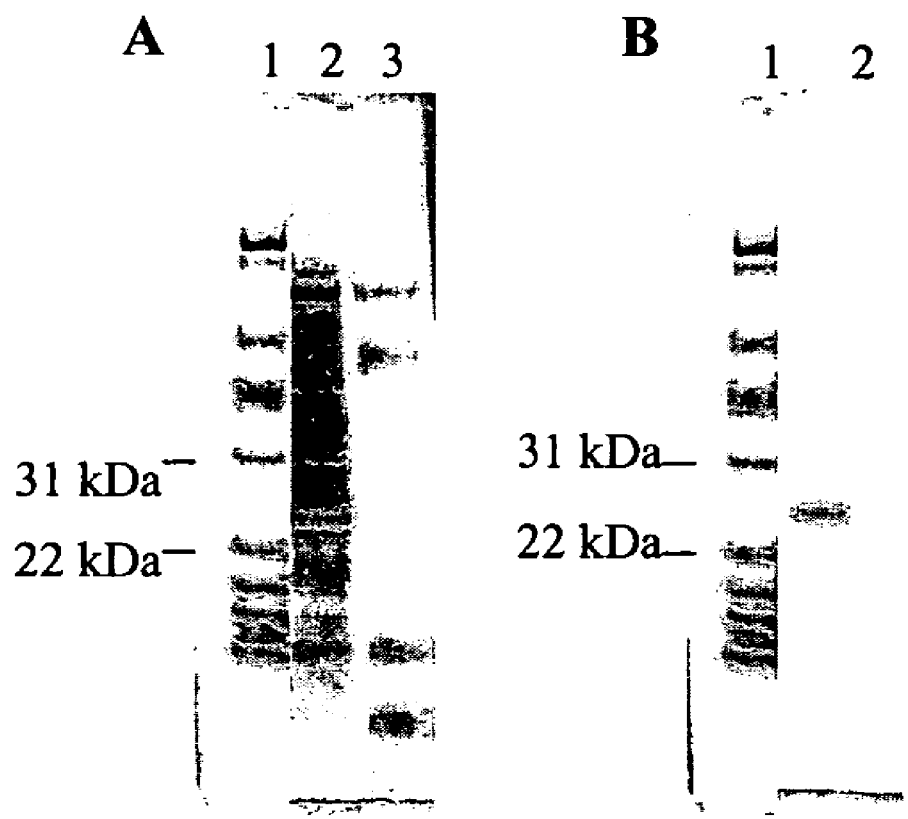
FIG. 1. Production of recombinant hK10 protein with the *Pichia pastoris* yeast expression system. The proteins were separated on SDS-PAGE and stained with coomassie blue. A: Lane 1, molecular weight markers; 2, culture supernatant obtained from a yeast clone transfected with pPIZαA vector containing KLK10 cDNA; 3, culture supernatant obtained from a yeast clone transfected with empty pPIZαA vector. B: Purified recombinant hK10 from the yeast expression system. Lane 1, molecular weight marker; 2, purified recombinant hK10. Purification was achieved with cation-exchange followed by reverse-phase chromatography. The intense band between markers of 31 and 22 kDa in lane 2 represents hK10.

As hereinbefore mentioned, the present invention provides a method for monitoring, diagnosing, or for the prognosis of ovarian carcinoma in a subject by detecting hK10 in a biological sample from the subject. In an embodiment, the method comprises reacting the sample with an antibody specific for hK610 which is directly or indirectly labelled with a detectable substance, and detecting the detectable substance.

The methods of the invention may be used for the detection of either an over- or an under-abundance of hK10 relative to a non-disorder state or the presence of a modified (e.g., less than full length) hK10 which correlates with a disorder state (e.g ovarian cancer), or a progression toward a disorder state. The methods described herein may be used to evaluate the probability of the presence of malignant or pre-malignant cells, for example, in a group of cells freshly removed from a host. Such methods can be used to detect tumors, quantitate their growth, and help in the diagnosis and prognosis of disease. The methods can be used to detect the presence of cancer metastasis, as well as confirm the absence or removal of all tumor tissue following surgery, cancer chemotherapy, and/or radiation therapy. They can further be used to monitor cancer chemotherapy and tumor reappearance.

The methods of the invention are particularly useful in the diagnosis of late stage ovarian cancer and for the prognosis of ovarian cancer disease progression and mortality. As illustrated herein increased levels of hK10 detected in a sample (e.g. serum, tumor tissues or extracts thereof) compared to a standard (e.g. levels for normal or benign issues) are indicative of advanced disease stage, serous histological type, suboptimal debulking, large residual tumor, and/or increased risk of disease progression and mortality.

The terms "sample", "biological sample", and the like mean a material known to or suspected of expressing or containing hK10. The test sample can be used directly as obtained from the source or following a pretreatment to modify the character of the sample. The sample can be derived from any biological source, such as tissues or extracts, including cells (e.g. tumor cells) and physiological fluids, such as, for example, whole blood, plasma, serum, saliva, ocular lens fluid, sweat, urine, milk, ascites fluid, synovial fluid, peritoneal fluid and the like. The sample can be obtained from animals, preferably manuals, most preferably humans. The sample can be treated prior to use, such as preparing plasma from blood, diluting viscous fluids, and the like. Methods of treatment can involve filtration, distillation, extraction, concentration, inactivation of interfering components, the addition of reagents, and the like.

The presence of hK10 may be detected in a variety of biological samples, including tissues or extracts thereof including, for example cells and fluids. Preferably, hK10 is detected in serum or human extracts, more preferably serum.

In embodiments of the invention, the method described herein is adapted for diagnosing and monitoring ovarian cancer by quantitating hK10 in biological samples from a subject. These applications require that the amount of hK10 quantitated in a sample from a subject being tested be compared to levels quantitated for another sample or an earlier sample from the subject, or levels quantitated for a control sample. Levels for control samples from healthy subjects may be established by prospective and/or retrospective statistical studies. Healthy subjects who have no clinically evident disease or abnormalities may be selected for statistical studies. Diagnosis may be made by a finding of statistically different levels of hK10 compared to a control sample or previous levels quantitated for the same subject.

The term "hK10" refers to human kallikrein 10, (also known as NES-1), a secreted serine protease, that has an amino acid sequence having 35-40% identity and 50-55% similarity with other members of the human kallikrein gene family, including PSA (9). The term includes all homologs, naturally occurring allelic variants, isoforms and precursors of human kallikrein 10 of GenBank Accession Nos. AAB81602 and NP_002767. In general for example, naturally occurring allelic variants of human kallikrein 10 will share significant homology (70-90%) to the sequences shown in GenBank Accession Nos. AAB81602 and NP_002767. Allelic variants may contain conservative amino acid substitutions from the KLK10 sequence (GenBank Accession Nos AF024605 and NM_002776) or will contain a substitution of an amino acid from a corresponding position in a hK10 homologue such as, for example, the murine kallikrein 10 homologue.

The term "subject" refers to a warm-blooded animal such as a mammal which is afflicted with ovarian cancer or condition as described herein. Preferably, "subject" refers to a human.

The antibodies specific for hK10 used in the methods of the invention may be obtained from scientific or commercial sources. Alternatively, isolated native hK10 or recombinant hK10 may be utilized to prepare antibodies, monoclonal or polyclonal antibodies, and immunologically active fragments (e.g. a Fab or (Fab)$_2$ fragment), an antibody heavy chain, an antibody light chain, humanized antibodies, a genetically engineered single chain $F_v$ molecule (Ladner et al, U.S. Pat. No. 4,946,778), or a chimeric antibody, for example, an antibody which contains the binding specificity of a murine antibody, but in which the remaining portions are of human origin. Antibodies including monoclonal and polyclonal antibodies, fragments and chimeras, may be prepared using methods known to those skilled in the art. Preferably, antibodies used in the methods of the invention are reactive against hK10 if they bind with a $K_a$ of greater than or equal to $10^{-7}$ M. In a sandwich immunoassay of the invention mouse polyclonal antibodies and rabbit polyclonal antibodies are utilized.

Antibodies specifically reactive with hK10, or derivatives, such as enzyme conjugates or labeled derivatives, may be used to detect hK10 in various biological samples, for example they may be used in any known immunoassays which rely on the binding interaction between an antigenic determinant of a protein and the antibodies. Examples of such assays are radioimmunoassays, enzyme immunoassay (e.g. ELISA), immunofluorescence, immunoprecipitation, latex agglutination, hemagglutination, and histochemical tests.

An antibody specific for hK10 may be labelled with a detectable substance and localized in biological samples based upon the presence of the detectable substance. Examples of detectable substances include, but are not limited to, the following radioisotopes (e.g $^3$H, $^{14}$C, $^{35}$S, $^{125}$I, $^{131}$I), fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinesterase), biotinyl groups (which can be detected by marked avidin e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags). Indirect methods may also be employed in which the primary antigen-antibody reaction is amplified by the introduction of a second antibody, having specificity for the antibody reactive against hK10. By way of example, if the antibody having specificity against hK10 is a rabbit IgG antibody, the second antibody may be goat anti-rabbit gammaglobulin labelled with a detectable substance as described herein.

Methods for conjugating or labelling the antibodies discussed above may be readily accomplished by one of ordinary skill in the art. (See for example Inman, Methods In Enzymology, Vol. 34, Affinity Techniques, Enzyme Purification: Part B, Jakoby and Wichek (eds.), Academic Press, New York, p. 30, 1974; and Wilchek and Bayer, "The Avidin-Biotin Complex in Bioanalytical Applications," Anal. Biochem. 171:1-32, 1988 re methods for conjugating or labelling the antibodies with enzyme or ligand binding partner).

Time-resolved fluorometry may be used to detect a signal. For example, the method described in Christopoulos T K and Diamandis E P Anal Chem 1992:64:342-346 may be used with a conventional time-resolved fluorometer.

Therefore, in accordance with an embodiment of the invention, a method is provided wherein a hK10 antibody is labelled with an enzyme, a substrate for the enzyme is added wherein the substrate is selected so that the substrate, or a reaction product of the enzyme and substrate, forms fluorescent complexes with a lanthanide metal. A lanthanide metal is added and hK10 is quantitated in the sample by measuring fluorescence of the fluorescent complexes. The antibodies specific for hK10 may be directly or indirectly labelled with an enzyme. Enzymes are selected based on the ability of a substrate of the enzyme, or a reaction product of the enzyme and substrate, to complex with lanthanide metals such as europium and terbium. Examples of suitable enzymes include alkaline phosphatase and β-galactosidase. Preferably, the enzyme is alkaline phosphatase. The hK10 antibodies may also be indirectly labelled with an enzyme. For example, the antibodies may be conjugated to one partner of a ligand binding pair, and the enzyme may be coupled to the other partner of the ligand binding pair. Representative examples include avidin-biotin, and riboflavin-riboflavin binding protein. Preferably the antibodies are biotinylated, and the enzyme is coupled to streptavidin.

In the method, antibody bound to hK10 in a sample is detected by adding a substrate for the enzyme. The substrate is selected so that in the presence of a lanthanide metal (e.g. europium, terbium, samarium, and dysprosium, preferably europium and terbium), the substrate or a reaction product of the enzyme and substrate, forms a fluorescent complex with the lanthanide metal. Examples of enzymes and substrates for enzymes that provide such fluorescent complexes are described in U.S. Pat. No. 5,312,922 to Diamandis. By way of example, when the antibody is directly or indirectly labelled with alkaline phosphatase the substrate employed in the method may be 4-methylumbelliferyl phosphate, or 5-fluorosalicyl phosphate. The fluorescence intensity of the complexes is typically measured using a time-resolved fluorometer e.g. a CyberFluor 615 Imunoanalyzer (Nordion International, Kanata Ontario).

The sample, antibody specific for hK10, or hK10, may be immobilized. Examples of suitable carriers are agarose, cellulose, dextran, Sephadex, Sepharose, liposomes, carboxymethyl cellulose polystyrene, filter paper, ion-exchange resin, plastic film, plastic tube, glass beads, polyamine-methyl vinyl ether-maleic acid copolymer, amino acid copolymer, ethylene-maleic acid copolymer, nylon, silk, etc. The carrier may be in the shape of, for example, a tube, test plate, well, beads, disc, sphere etc. The immobilized antibody may be prepared by reacting the material with a suitable insoluble carrier using known chemical or physical methods, for example, cyanogen bromide coupling.

In accordance with an embodiment, the present invention provides means for determining hK10 in a blood sample by measuring hK10 by immunoassay. It will be evident to a skilled artisan that a variety of immunoassay methods can be used to measure hK10. In general, an hK10 immunoassay method may be competitive or noncompetitive. Competitive methods typically employ an immobilized or immobilizable antibody to hK10 (anti-hK10) and a labeled form of hK10. Sample hK10 and labeled hK10 compete for binding to anti-hK10. After separation of the resulting labeled hK10 that has become bound to anti-hK10 (bound fraction) from that which has remained unbound (unbound fraction), the amount of the label in either bound or unbound fraction is measured and may be correlated with the amount of hK10 in the test sample in any conventional manner, e.g., by comparison to a standard curve.

Preferably a noncompetitive method is used for the determination of hK10, with the most common method being the "sandwich" method. In this assay, two anti-hK10 antibodies are employed. One of the anti-hK10 antibodies is directly or indirectly labeled (sometimes referred to as the "detection antibody") and the other is immobilized or immobilizable (sometimes referred to as the "capture antibody"). The capture and detection antibodies can be contacted simultaneously or sequentially with the test sample. Sequential methods can be accomplished by incubating the capture antibody with the sample, and adding the detection antibody at a predetermined time thereafter (sometimes referred to as the "forward" method); or the detection antibody can be incubated with the sample first and then the capture antibody added (sometimes referred to as the "reverse" method). After the necessary incubation(s) have occurred, to complete the assay, the capture antibody is separated from the liquid test mixture, and the label is measured in at least a portion of the separated capture antibody phase or the remainder of the liquid test mixture. Generally it is measured in the capture antibody phase since it comprises hK10 bound by ("sandwiched" between) the capture and detection antibodies.

In a typical two-site immunometric assay for hK10, one or both of the capture and detection antibodies are polyclonal antibodies. The label used in the detection antibody can be selected from any of those known conventionally in the art. The label may be an enzyme or a chemiluminescent moiety, but it can also be a radioactive isotope, a fluorophor, a detectable ligand (e.g., detectable by a secondary binding by a labeled binding partner for the ligand), and the like. Preferably, the antibody is labeled with an enzyme which is detected by adding a substrate that is selected so that a reaction product of the enzyme and substrate forms fluorescent complexes. The capture antibody is selected so that it provides a means for being separated from the remainder of the test mixture. Accordingly, the capture antibody can be introduced to the assay in an already immobilized or insoluble form, or can be in a immobilizable form, that is, a form which enables immobilization to be accomplished subsequent to introduction of the capture antibody to the assay. An immobilized capture antibody may comprise an antibody covalently or noncovalently attached to a solid phase such as a magnetic particle, a latex particle, a microtiter plate well, a bead, a cuvette, or other reaction vessel. An example of an immobilizable capture antibody is antibody which has been chemically modified with a ligand moiety, e.g., a hapten, biotin, or the like, and which can be subsequently immobilized by contact with an immobilized form of a binding partner for the ligand, e.g., an antibody, avidin, or the like. In an embodiment, the capture antibody may be immobilized using a species specific antibody for the capture antibody that is bound to the solid phase.

A particular sandwich immunoassay method of the invention employs two antibodies reactive against hK10, a second antibody having specificity against an antibody reactive against hK10 labelled with an enzymatic label, and a fluorogenic substrate for the enzyme. In an embodiment, the enzyme is alkaline phosphatase (ALP) and the substrate is 5-fluorosalicyl phosphate. ALP cleaves phosphate out of the fluorogenic substrate, 5-fluorosalicyl phosphate, to produce 5-fluorosalicylic acid (FSA). 5-Fluorosalicylic acid can then form a highly fluorescent ternary complex of the form FSA-Tb(3+)-EDTA, which can be quantified by measuring the Tb3+ fluorescence in a time-resolved mode. Fluorescence intensity is typically measured using a time-resolved fluorometry as described herein.

The above-described immunoassay methods and formats are intended to be exemplary and are not limiting since, in general, it will be understood that any immunoassay method or format can be used in the present invention.

The methods of the invention can be carried out using a diagnostic kit for quantitating hK10 in a sample. By way of example, the kit may contain antibodies specific for hK10, antibodies against the antibodies labelled with an enzyme; and a substrate for the enzyme. The kit may also contain microtiter plate wells, standards, assay diluent, wash buffer, adhesive plate covers, and/or instructions for carrying out a method of the invention using the kit.

Antibodies specific for hK10 may also be used in imaging methodologies in the management of ovarian cancer. The invention provides a method for imaging tumors associated with hK10.

The invention also contemplates imaging methods described herein using multiple markers for ovarian cancer. For example, a method for imaging ovarian cancer may further comprise using one or more of an agent that binds to human stratum corneum chymotryptic enzyme (HSCCE), kallikrein 4, kallikrein 5, kallikrein 6, kallikrein 8, and kallikrein 9, CA125, CA15-3, CA19-9, OVX1, lysophosphatidic acid (LPA) or carcinoembryonic antigen (CEA), preferably CA 125. Preferably each agent is labeled so that it can be distinguished during the imaging.

In an embodiment the method is an in vivo method and a subject or patient is administered one or more agents that carry an imaging label and that are capable of targeting or binding to a kallikrein. The agent is allowed to incubate in vivo and bind to the kallikrein(s) associated with a tumor, preferably ovarian tumors. The presence of the label is localized to the ovarian cancer, and the localized label is detected using imaging devices known to those skilled in the art.

The agent may be an antibody or chemical entity which recognizes the kallikrein(s). In an aspect of the invention the agent is a polyclonal antibody or monoclonal antibody, or fragments thereof, or constructs thereof including but not limited to, single chain antibodies, bifunctional antibodies, molecular recognition units, and peptides or entities that mimic peptides. The antibodies specific for the kallikreins used in the methods of the invention may be obtained from scientific or commercial sources, or isolated native kallikrein or recombinant kallikrein may be utilized to prepare antibodies etc as described herein.

An agent may be a peptide that mimics the epitope for an antibody specific for a kallikrein and binds to the kallikrein. The peptide may be produced on a commercial synthesizer using conventional solid phase chemistry. By way of example, a peptide may be prepared that includes either tyrosine lysine, or phenylalanine to which $N_2S_2$ chelate is complexed (See U.S. Pat. No. 4,897,255). The anti-kallikrein peptide conjugate is then combined with a radiolabel (e.g. sodium $^{99m}Tc$ pertechnetate or sodium $^{188}Re$ perrhenate) and it may be used to locate a kallikrein producing tumor.

The agent carries a label to image the kallikrein. The agent may be labelled for use in radionuclide imaging. In particular, the agent may be directly or indirectly labelled with a radioisotope. Examples of radioisotopes that may be used in the present invention are the following: $^{277}Ac$, $^{211}At$, $^{128}Ba$, $^{131}Ba$, $^{7}Be$, $^{204}Bi$, $^{205}Bi$, $^{206}Bi$, $^{76}Br$, $^{77}Br$, $^{82}Br$, $^{109}Cd$, $^{47}Ca$, $^{11}C$, $^{14}C$, $^{36}Cl$, $^{48}Cr$, $^{51}Cr$, $^{62}Cu$, $^{64}Cu$, $^{67}Cu$, $^{165}Dy$, $^{155}Eu$, $^{18}F$, $^{153}Gd$, $^{66}Ga$, $^{67}Ga$, $^{68}Ga$, $^{72}Ga$, $^{198}Au$, $^{3}H$, $^{166}Ho$, $^{111}In$, $^{113m}In$, $^{115m}In$, $^{123}I$, $^{125}I$, $^{131}I$, $^{189}I$, $^{191m}Ir$, $^{192}Ir$, $^{194}Ir$, $^{52}Fe$, $^{55}Fe$, $^{59}Fe$, $^{177}Lu$, $^{15}O$, $^{191m-191}Os$, $^{109}Pd$, $^{32}P$, $^{33}P$, $^{42}K$, $^{226}Ra$, $^{186}Re$, $^{188}Re$, $^{82m}Rb$, $^{153}Sm$, $^{46}Sc$, $^{47}Sc$, $^{72}Se$, $^{75}Se$, $^{105}Ag$, $^{22}Na$, $^{24}Na$, $^{89}Sr$, $^{35}S$, $^{38}S$, $^{177}Ta$, $^{96}Tc$, $^{99m}Tc$, $^{201}Tl$, $^{202}Tl$, $^{113}Sn$, $^{117m}Sn$, $^{121}Sn$, $^{166}Yb$, $^{169}Yb$, $^{175}Yb$, $^{88}Y$, $^{90}Y$, $^{62}Zn$ and $^{65}Zn$. Preferably the radioisotope is $^{131}I$, $^{125}I$, $^{123}I$, $^{111}I$, $^{99m}Tc$, $^{90}Y$, $^{186}Re$, $^{188}Re$, $^{32}P$, $^{153}Sm$, $^{67}Ga$, $^{201}Tl$ $^{77}Br$, or $^{18}F$, and is imaged with a photoscanning device.

Procedures for labeling biological agents with the radioactive isotopes are generally known in the art. U.S. Pat. No. 4,302,438 describes tritium labeling procedures. Procedures for iodinating, tritium labeling, and $^{35}S$ labeling especially adapted for murine monoclonal antibodies are described by Goding, J. W. (supra, pp 124-126) and the references cited therein. Other procedures for iodinating biological agents, such as antibodies, binding portions thereof, probes, or ligands, are described in the scientific literature (see Hunter and Greenwood, Nature 144:945 (1962), David et al., Biochemistry 13:1014-1021 (1974), and U.S. Pat. Nos. 3,867, 517 and 4,376,110). Iodinating procedures for agents are described by Greenwood, F. et al., Biochem. J. 89:114-123 (1963); Marchalonis, J., Biochem. J. 113:299-305 (1969); and Morrison, M. et al., Immunochemistry, 289-297 (1971). $^{99m}Tc$-labeling procedures are described by Rhodes, B. et al. in Burchiel, S. et al. (eds.), Tumor Imaging: The Radioimmunochemical Detection of Cancer, New York: Masson 111-123 (1982) and the references cited therein. Labelling of antibodies or fragments with technetium-99m are also described for example in U.S. Pat. No. 5,317,091, U.S. Pat. No. 4,478,815, U.S. Pat. No. 4,478,818, U.S. Pat. No. 4,472,371, U.S. Pat. No. Re 32,417, and U.S. Pat. No. 4,311,688. Procedures suitable for $^{111}In$-labeling biological agents are described by Hnatowich, D. J. et al., J. Immul. Methods, 65:147-157 (1983), Hnatowich, D. et al., J. Applied Radiation, 35:554-557 (1984), and Buckley, R. G. et al., F.E.B.S. 166:202-204 (1984).

An agent may also be labeled with a paramagnetic isotope for purposes of an in vivo method of the invention. Examples of elements that are useful in magnetic resonance imaging include gadolinium, terbium, tin, iron, or isotopes thereof. (See, for example, Schaefer et al., (1989) JACC 14, 472-480; Shreve et al., (1986) Magn. Reson. Med. 3, 336-340; Wolf, G L, (1984) Physiol. Chem. Phys. Med. NMR 16, 93-95; Wesbey et al., (1984) Physiol. Chem. Phys. Med. NMR 16, 145-155; Runge et al., (1984) Invest. Radiol. 19, 408-415 for discussions on in vivo nuclear magnetic resonance imaging.)

In the case of a radiolabeled agent, the agent may be administered to the patient, it is localized to the tumor having a kallikrein with which the agent binds, and is detected or "imaged" in vivo using known techniques such as radionuclear scanning using e.g., a gamma camera or emission tomography. [See for example A. R. Bradwell et al., "Developments in Antibody Imaging", Monoclonal Antibodies for Cancer Detection and Therapy, R. W. Baldwin et al., (eds.), pp. 65-85 (Academic Press 1985)]. A positron emission transaxial tomography scanner, such as designed Pet VI located at Brookhaven National Laboratory, can also be used where the radiolabel emits positrons (e.g., $^{11}C$, $^{18}F$, $^{15}O$, and $^{13}N$).

Whole body imaging techniques using radioisotope labeled agents can be used for locating both primary tumors and tumors which have metastasized. Antibodies specific for kallikreins, or fragments thereof having the same epitope specificity, are bound to a suitable radioisotope, or a combination thereof, and administered parenterally. For ovarian cancer, administration on preferably is intravenous. The biodistribution of the label can be monitored by scintigraphy, and accumulations of the label are related to the presence of ovarian cancer cells. Whole body imaging techniques are described in U.S. Pat. Nos. 4,036,945 and 4,311,688. Other examples of agents useful for diagnosis and therapeutic use which can be coupled to antibodies and antibody fragments include metallothionein and fragments (see, U.S. Pat. No. 4,732,864). These agents are useful in diagnosis staging and visualization of cancer, in particular ovarian cancer, so that surgical and/or radiation treatment protocols can be used more efficiently.

The invention also contemplates kits for carrying out the methods of the invention. The kits include an antibody or an antibody fragment which binds specifically to an epitope of a kallikrein, and means for detecting binding of the antibody to its epitope associated with tumor cells, either as concentrates (including lyophilized compositions), which may be further diluted prior to use or at the concentration of use, where the vials may include one or more dosages. Where the kits are intended for in vivo use, single dosages may be provided in sterilized containers, having the desired amount and concentration of agents. Containers that provide a formulation for direct use, usually do not require other reagents, as for example, where the kit contains a radiolabeled antibody preparation for in vivo imaging.

The following non-limiting examples are illustrative of the present invention:

Example 1

Immunofluorometric Assay of Human Kallikrein 10

Materials and Methods

Production and Purification of Recombinant hK10

Cloning of KLK10 cDNA into the yeast expression vector. In order to produce recombinant hK10, the Easyselect™ *Pichia pastoris* yeast expression System (Invitrogen, Carlsbad, Calif.) was used. Two primers designed to amplify the KLK10 cDNA sequence encoding for amino acid 43 to 276 (The numbering of amino acids of hK10 is reported in ref. 8). They are as follows: forward primer 5'AACGACGAATTCT-TGGACCCCGAAGCT3' (SEQ ID NO. 1), reverse primer: 5' CGTAGAATTCGGATCAGTTGGA 3'(SEQ ID NO. 2). Human ovarian cDNA was used as template PCR was carried out in a 20 μL reaction mixture, containing 1 μL cDNA, 10 mM Tris-HCl (pH 83), 50 mM KCl, 15 mM $MgCl_2$, 200 μM dNTPs (deoxynucleoside triphosphates), 100 ng primers and 2.5 units of pfu DNA polymerase (Stratagene, La Jolla, Calif.) on a Perkin-Elmer 9600 thermal cycler. The PCR conditions were 94° C. for 5 minutes, followed by 30 cycles of 94° C. for 30 seconds 62° C. for 30 seconds, 72° C. for 30 seconds and a final extension at 72° C. for 5 minutes. The PCR product was then cloned into the yeast expression vector pPIZαA using standard molecular biology techniques (13).

Production of hK10 in yeast. pPIZαA vector containing the KLK10 cDNA was introduced into the yeast strain X-33 and a stable clone was selected following the manufacturer's instructions. hK10 was produced by growing the stable yeast clone in a medium containing 10 g/L yeast extract, 20 g/L peptone, 100 mM potassium phosphate (pH 6.0), 13.4 g/L yeast nitrogen base, 40 g/L biotin and 5 ml/L methanol in a 30° C. shaking incubator (250 rpm) for 5 days. The cells were then spun down and the supernatant was collected.

Purification of hK10 with cation-change chromatography and reversed-phase chromatography. The recombinant hK10 protein was purified from the yeast culture supernatant with cation-exchange chromatography using CM sepharose fast flow (Pharmacia, Piscataway, N.J.) and reversed-phase liquid chromatography using a C4 column (0.45×5 cm) (Vydac, Hesperia, Calif.). In brief, the CM sepharose beads previously activated with 1M KCl was equilibrated in 10 mM MES buffer (pH6.5). The yeast culture supernatant was first absorbed on CM sepharose beads by incubating at 4° C. overnight under agitation. The beads were then washed with 10 mM MES buffer (pH 6.5) and hK10 was eluted with 300 mM KCl in 10 mM MES buffer (pH 6.5). Trifluoroacetic acid (TEA) as ion-pairing agent was added into this eluate (final concentration 10 ml/L) and then loaded on a C4 column, equilibrated with 1 ml/L of trifluoroacetic acid in water. A linear gradient (1%/min) of acetonitrile in 1 ml/L TFA from 15 to 50% was then performed. hK10 eluted at 42% acetonitrile. The fraction containing hK10 was then immediately evaporated by SpeedVac (Savant Instruments Inc., Farmingdale, N.Y.). The purified material was then separated on a sodium dodecyl sulphate-polyacrylamide gel electrophoresis (SDS-PAGE) and stained with Coomassie Blue to assess its purity and its molecular weigh The protein concentration of the purified hK10 was determined by the bicinchoninic acid method (Pierce Chemical Co., Rockford, Ill.).

Identification of hK10 by Mass Spectrometry

Proteolytic digestion: Polyacrylamide gels were stained with Coomassie G-250 for visualization and selected bands were subsequently excised and destained with 30% acetonitrile in 100 mM ammonium bicarbonate. Each band was then reduced (10 mM dithiothreitol in 50 mM ammonium bicarbonate, pH 8.3) and allylated (55 mM iodoacetamide in 50 mM ammonium bicarbonate, pH 8.3) prior to overnight trypsin digestion (Promega, Madison, Wis.). Peptide fragments were then extracted with 5% acetic acid, evaporated to dryness on a Savant concentrator and reconstituted in 10 μL of 50% aqueous methanol (0.5% acetic acid).

Mass spectrometry: All nanoelectrospray mass spectrometry (nESMS) experiments were conducted on a Q-Star (PE/Sciex, Concord, Ont. Canada) hybrid quadrupole/time-of-flight instrument, for high resolution and on-line tandem mass spectrometric experiments (14). Conventional mass spectra were obtained by operating the quadrupole in a RF-only mode while a pusher electrode was pulsed (~7 kHz frequency) to transfer all ions to the time-of-flight analyzer. Tandem mass spectrometry experiments on tryptic peptides identified in survey scan were conducted using a nanoelectrospray source. Precursor ions were selected by the first quadrupole while a pusher electrode was pulsed (~7 kHz frequency) to transfer fragment ions formed in the R.F.-only quadrupole cell to the time-of-fight analyzer. Mass spectral resolution was typically 9,000-10,000. A scan duration of 1 s and 2 s was set for conventional and MS-MS mass spectral acquisition, respectively. Collisional activation was performed using nitrogen collision gas with typically a 30 V offset between the DC voltage of the entrance quadrupole and the R.F.-only quadrupole cell. Data were acquired and processed using LC Tune and Biomultiview programs from PE/Sciex.

Production of Polyclonal Antibodies Against hK10

The purified recombinant hK10 was used as an immunogen to immunize rabbits and mice. 100 μg of hK10 were subcutaneously injected into female Balb/c nice and New Zealand white rabbits. The protein was diluted 1:1 in complete Freund's adjuvant for the first injection and in incomplete Freund's adjuvant for the subsequent injections. Injections were repeated every 3 weeks for six times Blood was drawn from the animals and tested for antibody generation. To test for production of anti-hK10 polyclonal antibodies, the following immunoassay was used. Sheep anti-mouse or goat anti-rabbit IgG (Jackson Immunoresearch, West Grove, Pa.) was immobilized on 96-well white ELISA plates. The mouse/rabbit serum was then applied to the plates in different dilutions ranging from 1:500 to 1:50,000. Biotinylated recombinant hK10 was then added (5-10 ng/well). Finally, alkaline phosphatase-conjugated streptavidin was added and the alkaline phosphatase activity was detected with time-resolved fluorescence (for more details, see below).

Immunofluorometric Assay for hK10

Standard assay procedure. White polystyrene microtiter plates were coated with sheep anti-mouse IgG, Fc fragment-specific antibody (Jackson Immunoresearch) by incubating overnight 100 μL/500 ng/well of coating antibody diluted in a 50 mmol/L Tris buffer, pH 7.80. The plates were then washed six times with the washing buffer (containing 9 g/L NaCl and 0.5 g/L Tween 20 in 10 mmol/L Tris buffer, pH 7.40). Mouse anti-hK10 antiserum was diluted 5,000 fold in a general diluent (containing 60 g/L BSA, 50 mmol/L Tris, pH 7.80, and 0.5 kg/L sodium azide) and 100 μL was applied to each well. After 1 hour incubation, the plates were washed six times with washing buffer. 100 μL of hK10 standards or samples were pipetted into each well and incubated for 1 hour with shading and then washed with washing buffer for six times. Subsequently, 100 μL of rabbit anti-hK10 antiserum diluted 5,000 fold in buffer A (containing the components of the general diluent plus 25 mL normal mouse serum, 100 mL normal goat serum and log bovine IgG per liter) was applied to each well, incubated for 30 minutes and washed as above. Finally, the plates were incubated with 100 μL per well of alkaline phosphatase-conjugated goat anti-rabbit IgG Fc fragment-specific (Jackson Immunoresearch) diluted 3,000 fold in buffer A for 30 minutes and washed as described above. 100 μL of 1 mM diflunisal phosphate (DFP) diluted in substrate buffer (0.1 M Tris, pH 9.1, 0.1 M NaCl and 1 mM $MgCl_2$) was added into each well and incubated for 10 minutes. 100 μL of developing solution (1M Tris base, 0.4 M NaOH, 2 mM $TbCl_3$, and 3M EDTA) was pipetted into each well and mixed for 1 minute. The fluorescence was measured with a time-resolved fluorometer, the Cyberfluor 615 Immunoanalyzer (MDS Nordion, Kanata, ON, Canada). The calibration and data reduction were performed automatically. For more details on these procedures, see Christopoulos T K and Diamandis E P., Anal Chem 1992; 64:342-6.

Determination of the sensitivity of the hK10 immunoassay. Recombinant hK10 was used to generate the standard curve. Various hK10 standards were prepared by diluting the purified recombinant hK10 in the general diluent.

These standards were used to define the detection limit of the assay.

Determination of the specificity of the hK10 immunoassay. Milk and seminal plasma samples and recombinant hK10 were used to determine the specificity of the developed immunoassay. These samples were first measured with the standard assay procedure described above. The mouse and rabbit anti-hK10 antisera were then successively replaced with sera from the same animals, obtained before immunization (preimmune sera). The samples were then measured again and the fluorescence counts were compared with the counts obtained by the standard assay. The cross-reactivity of other homologous proteins was investigated by using purified recombinant PSA, hK2 and hK6 (available in-house). Recombinant hK10 (ranging from 0.025 to 2 ng), PSA (ranging from 20 ng to 1 μg), hK2 (ranging from 2 to 10 ng) and hK6 (ring from 11 to 55 ng) were used as samples, measured with the standard procedure described above and their fluorescence counts were compared (all specified amounts refer to mass of analyte per assay).

Linearity of the hK10 immunoassay. To determine the linearity of the hK10 immunoassay, various clinical samples were serially diluted 2, 4, 8, 16, and 32-fold in general diluent and their hK10 concentrations were measured with the standard assay.

Human Tissue Cytosolic Extracts and Biological Fluids

Human tissue cytosolic extracts were prepared as follows: Various frozen human tissues (0.2 g) were pulverized on dry ice to fine powders. One ml of extraction buffer (50 mM Tris, pH 8.0, 150 mM NaCl, 5 mM EDTA, 10 g/L of NP-40 surfactant, 1 mM PMSF, 1 g/L of aprotinin, 1 g/L of leupeptin) was added to the tissue powders and incubated on ice for 30 minutes with repeated shaking and vortexing every ten minutes. Mixtures were then centrifuged at 14,000 rpm at 4° C. for 30 minutes. The supernatants (cytosolic extracts) were then collected. The biological fluids were leftovers of samples submitted for routine biochemical testing. All tissue cytosolic extracts and biological fluids were stored at −80° C. until use.

Recovery

Recombinant hK10 was added to the general diluent, serum, cerebrospinal fluid, breast milk, seminal plasma, and amniotic fluid at different concentrations and measured with the developed hK10 immunoassay. Recovery was then calculated after subtracting the originally sent concentration.

Fractionation of Biological Fluids with Size-exclusion High Performance Liquid Chromatography Serum, milk and seminal plasma were fractionated with a silica-based gel filtration column essentially as described elsewhere (Yu H and Dimandis E P., Clin Chem 1993; 39:2108-14.). The fractions were collected and analyzed for hK10 with the developed immunoassay.

Results

Figure 2:
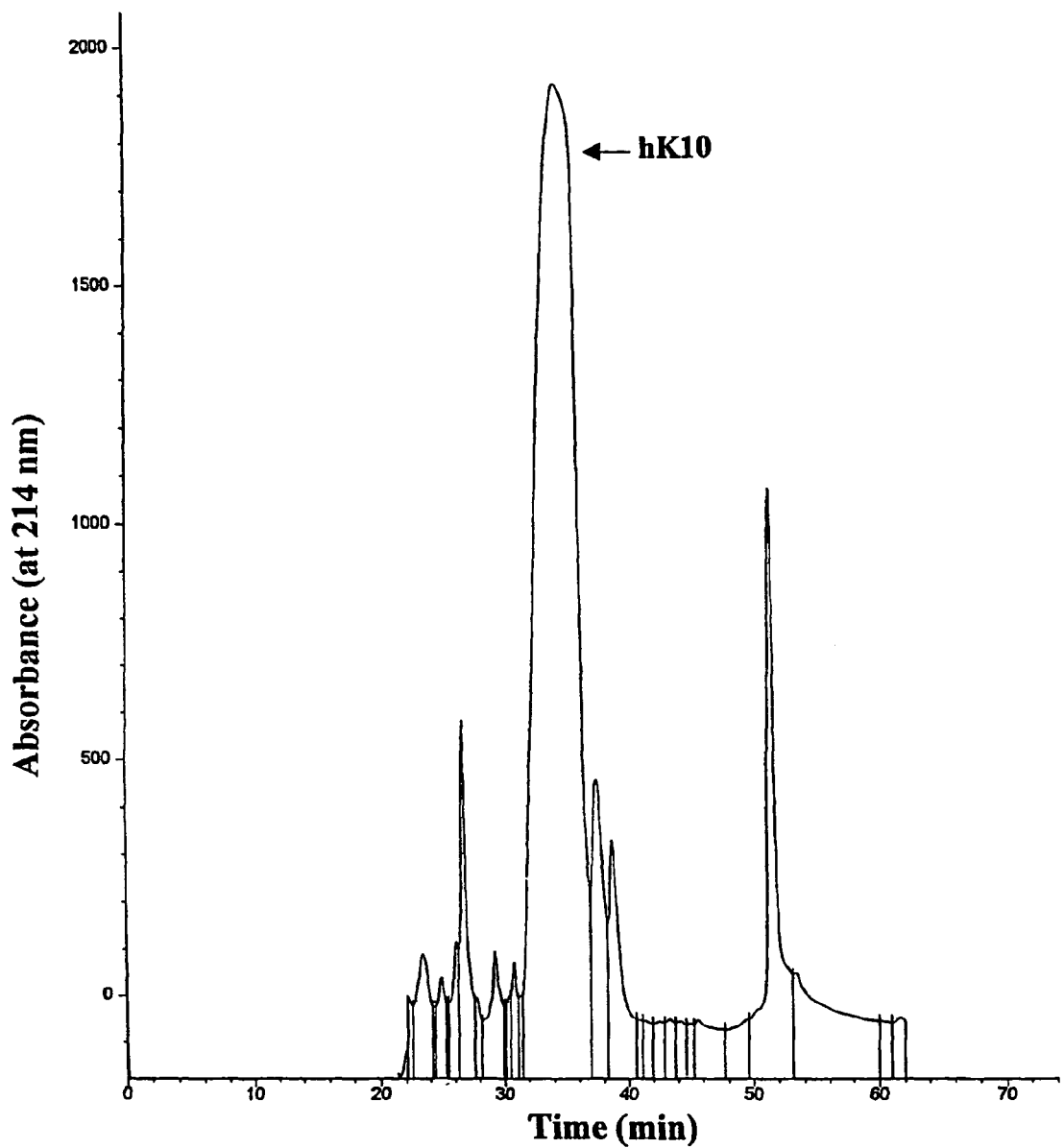
FIG. 2. A typical chromatogram showing the purification of recombinant hK10 from yeast culture supernatant with reversed-phase HPLC. Recombinant hK10 elutes around 35 min (41-42% acetonitrile).
Figure 3:
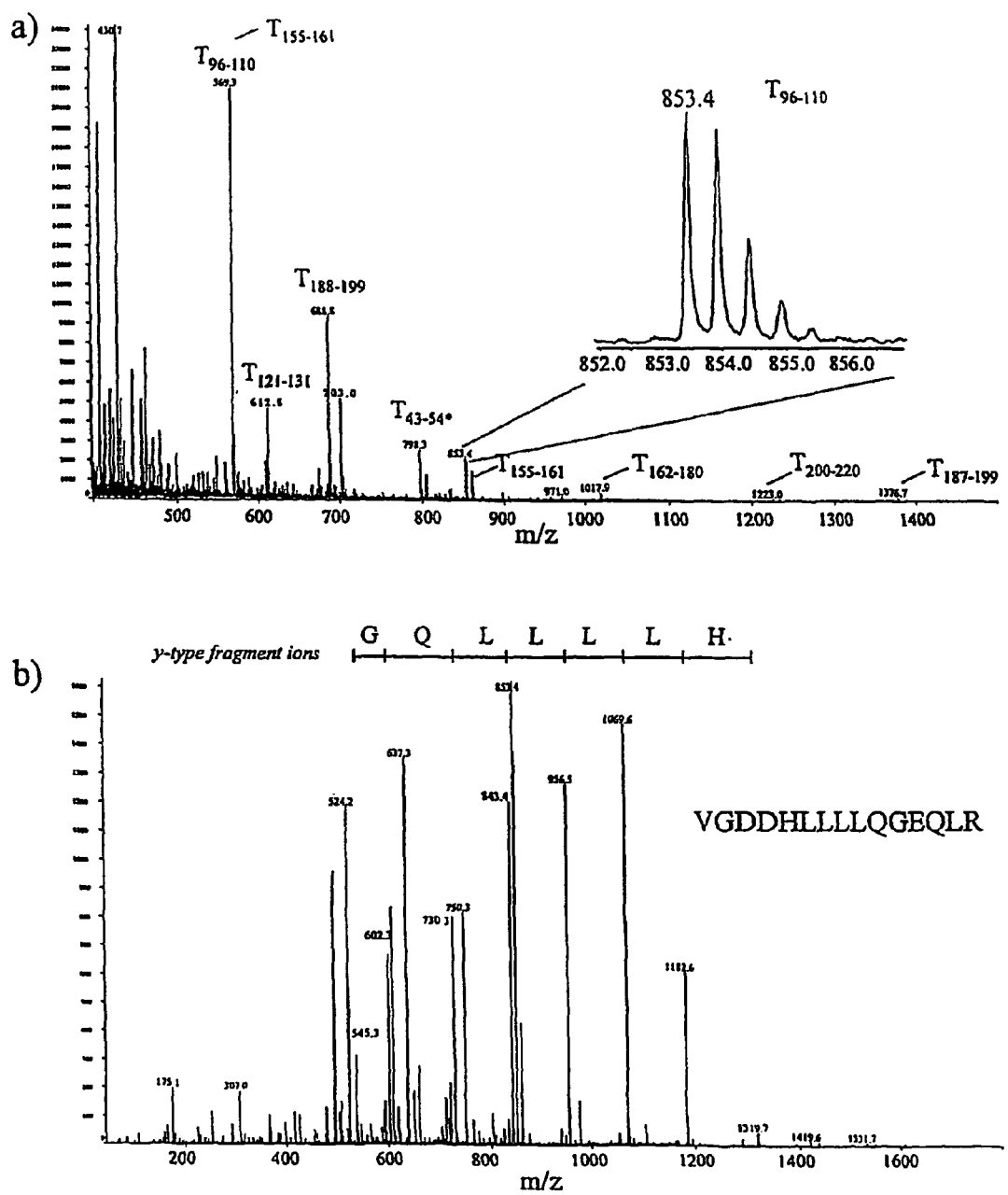
FIG. 3. Mass spectral characterization of hK10 and its tryptic peptides isolated from the band identified in lane 2, FIG. 1B. (a). Nanoelectrospray mass spectrum of gel-extracted peptides. Product ion spectrum of precursor m/z 853.4 using a collision energy of 30 V offset, $N_2$ target gas. (b). The y-type fragment ions refer to cleavage of peptide bond with charge retention on C-terminus end (Roepstorff P and Fohlman J. Biomed Mass Spectrom 1984; 11:601. [letter]). Amino acids are annotated using single-letter code. The peptide sequence VGDDHLLLLQGEQLR SE ID NO: 3 represents amino acids 96-110 of the hK10 sequence, as reported in Ref. 8.

Production and Purification of hK10 Recombinant Protein hK10 is a secreted serine protease. Hydrophobicity and structural homology analysis suggested that the active form of hK10 was predicted to start from amino acid 43 [the segment 1-42 represses the signal peptide (33 amino acids) and the activation peptide (9 amino acid)] (Liu X L, Wazer D E, Watanabe K and Band V., Cancer Res 1996; 56:3371-9). The cDNA encoding for this active form of hK10 was cloned into a *Pichia pastoris* yeast expression system. The 26 kDa recombinant hK10 protein was produced and secreted into the yeast culture supernatant (FIG. 1A), then purified with cation-change and reversed-phase chromatography (FIGS. 1B and 2). The sequence of this recombinant protein was verified by mass spectrometry (FIG. 3).

Figure 4:
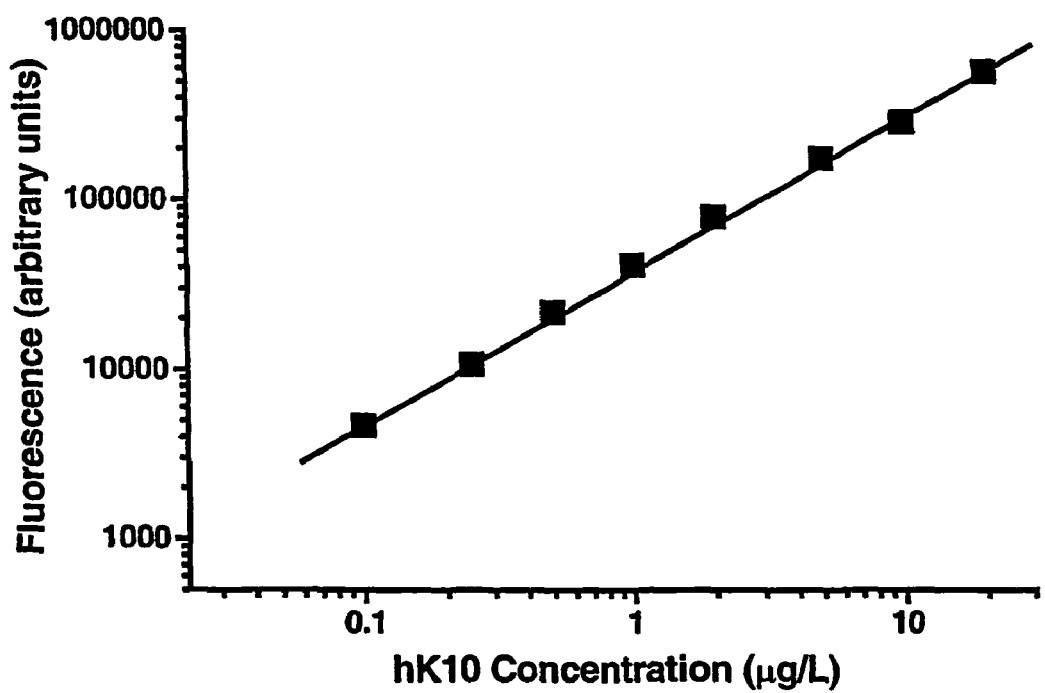
FIG. 4. A typical calibration curve of the hK10 immunoassay. The background fluorescence (zero calibrator) has been subtracted from all other measurements. The dynamic range of the assay is 0.05-20 µg/L.

Sensitivity, Specificity, Linearity, and Precision of the hK10 Immunofluorometric Assay Specificity. A typical calibration curve of the hK10 Immunofluorometric procedure is shown in FIG. 4. The detection limit defined as the concentration corresponding to the fluorescence of the zero calibrator plus two standard deviations, is 0.05 μg/L.

Figure 5:
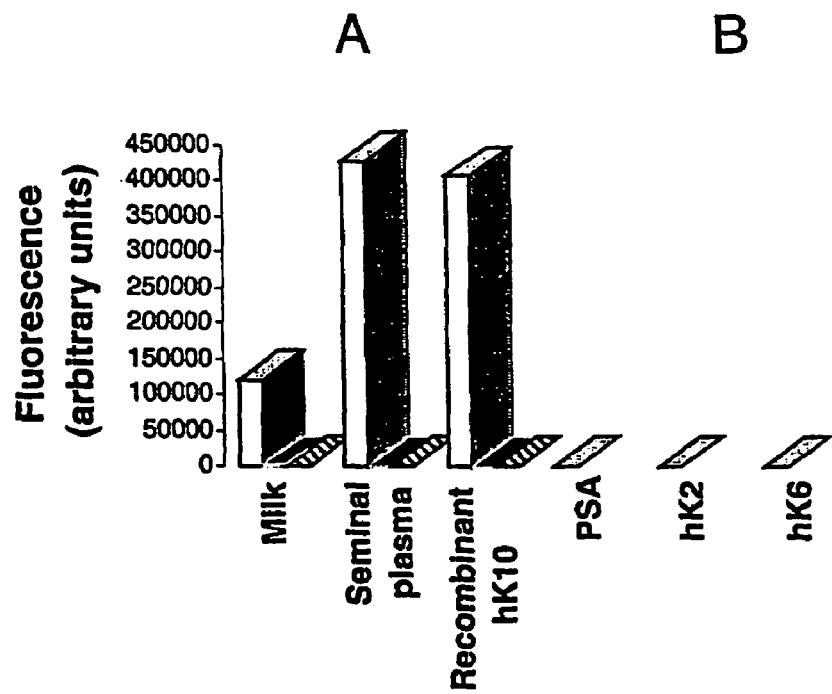
FIG. 5. Bar diagram showing the specificity of the hK10 immunoassay and the cross-reaction between hK10 and PSA, hK2, and hK6. A: ☐ mouse and rabbit anti-hK10 antisera; ■ preimmune mouse serum plus rabbit anti-hK10 antiserum; ◩ mouse anti-hK10 antiserum plus preimmune rabbit serum. Note the absence of immunoreactivity when the hK10 antisera are replaced with preimmune sera. B: Cross-reactivity of PSA, hK10 and hK6 with the standard hK10 immunoassay. No detectable cross-reactivity was found.

Specificity. In order to ensure that the immunoassays measures hK10 specifically, mouse and rabbit anti-hK10 antisera were replace with preimmune mouse and rabbit serum, respectively. Milk and seminal plasma samples and recombinant hK10 were measure. With the standard procedure, these samples all produced remotely high counts (>100,000 arbitrary fluorescence units). However, when either mouse or rabbit anti-hK10 polyclonal antibodies were replaced with preimmune serum, the fluorescence counts of these samples were reduced almost to zero (FIG. 5). Since hK10 is a member of the human kallikrein gene family, it shares significant amino acid sequence homology with other members. To further demonstrate that their is no interference from these homologous proteins, the cross-reactivity of hK10, PSA, hK2, and hK6 was examined. As FIG. 5 shows, when recombinant PSA, hK2 and hK6 were measured with the developed standard hK10 assay, they produced no counts even when they were present at amounts 5-500 times higher than hK10. These results suggest that their immunoassay can discriminate efficiently hK10 from other highly homologous proteins and that it measures hK10 in high specificity.

Figure 6:
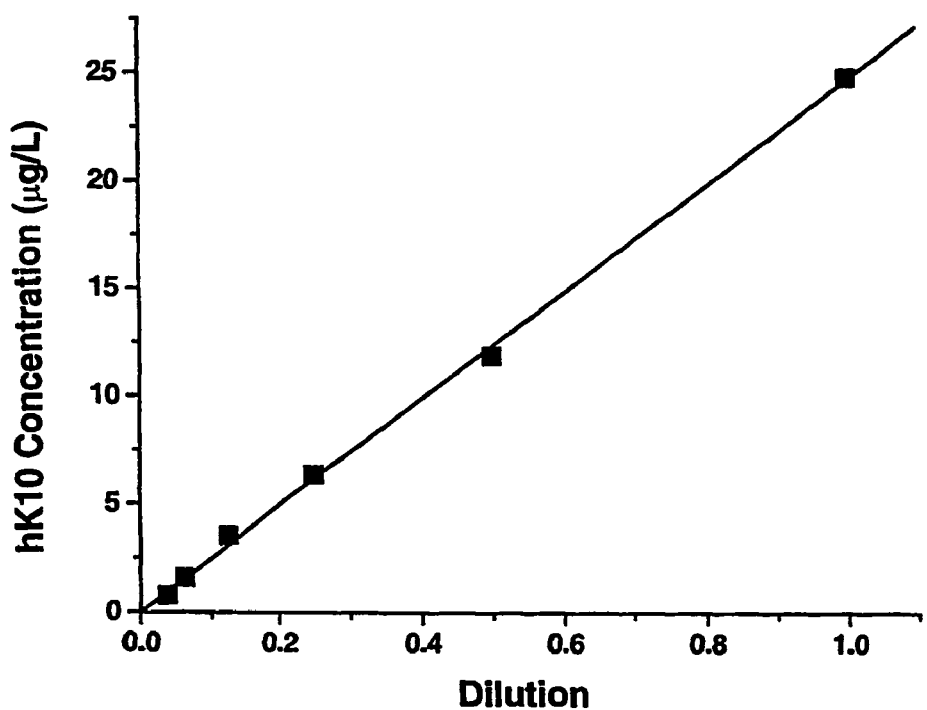
FIG. 6. Linearity of the hK10 immunoassay. A seminal plasma sample (an example of various clinical samples tested) was serially diluted 2, 4, 8, 16, and 32-fold. Linear regression was performed (r=0.999, slope=24.64). There is an excellent dilution linearity with the hK10 immunoassay.

Linearity. To assess the linearity of this assay, various samples were diluted serially and hK10 was measured. An example is shown in FIG. 6. There is excellent dilution linearity with this assay.

Precision. Within-run and between-run precision was assessed with various hK10 standards and clinical samples. In all cases, the coefficients of variation (CVs) were between 2-9%, consistent with the precision of typical microtiter plate-based immunoassays (data not shown).

Distribution of hK10 in Various Human Tissue Extracts and Biological Fluids

Figure 7:
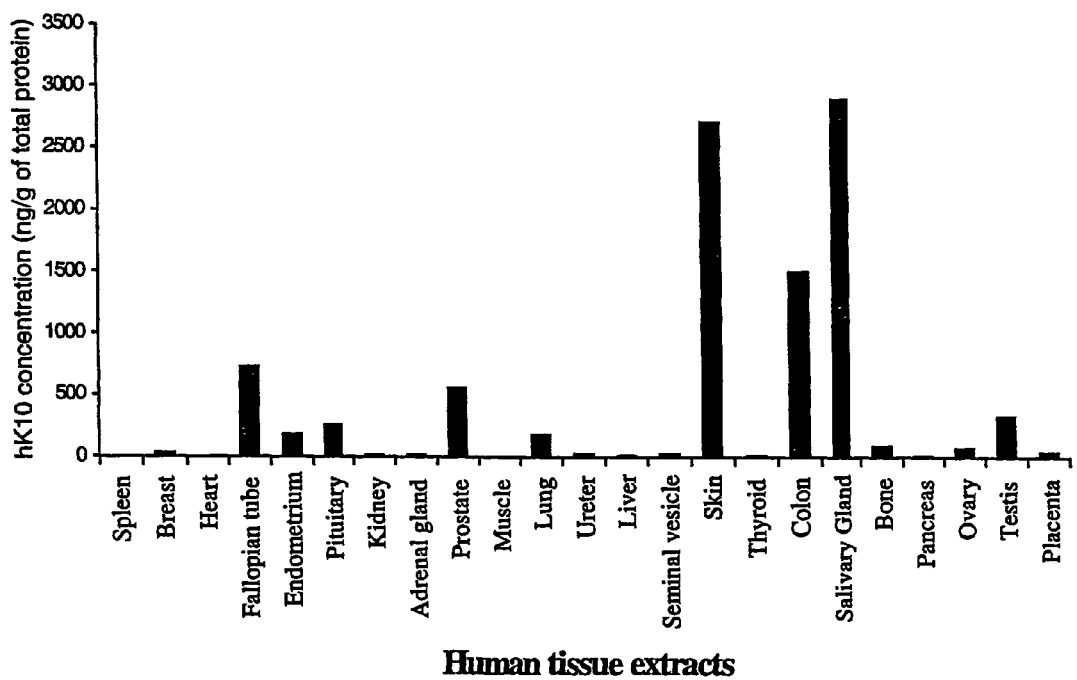
FIG. 7. Content of hK10 (in ng of hK10 per g of total protein) in cytosolic extracts from various human tissues.
Figure 8:
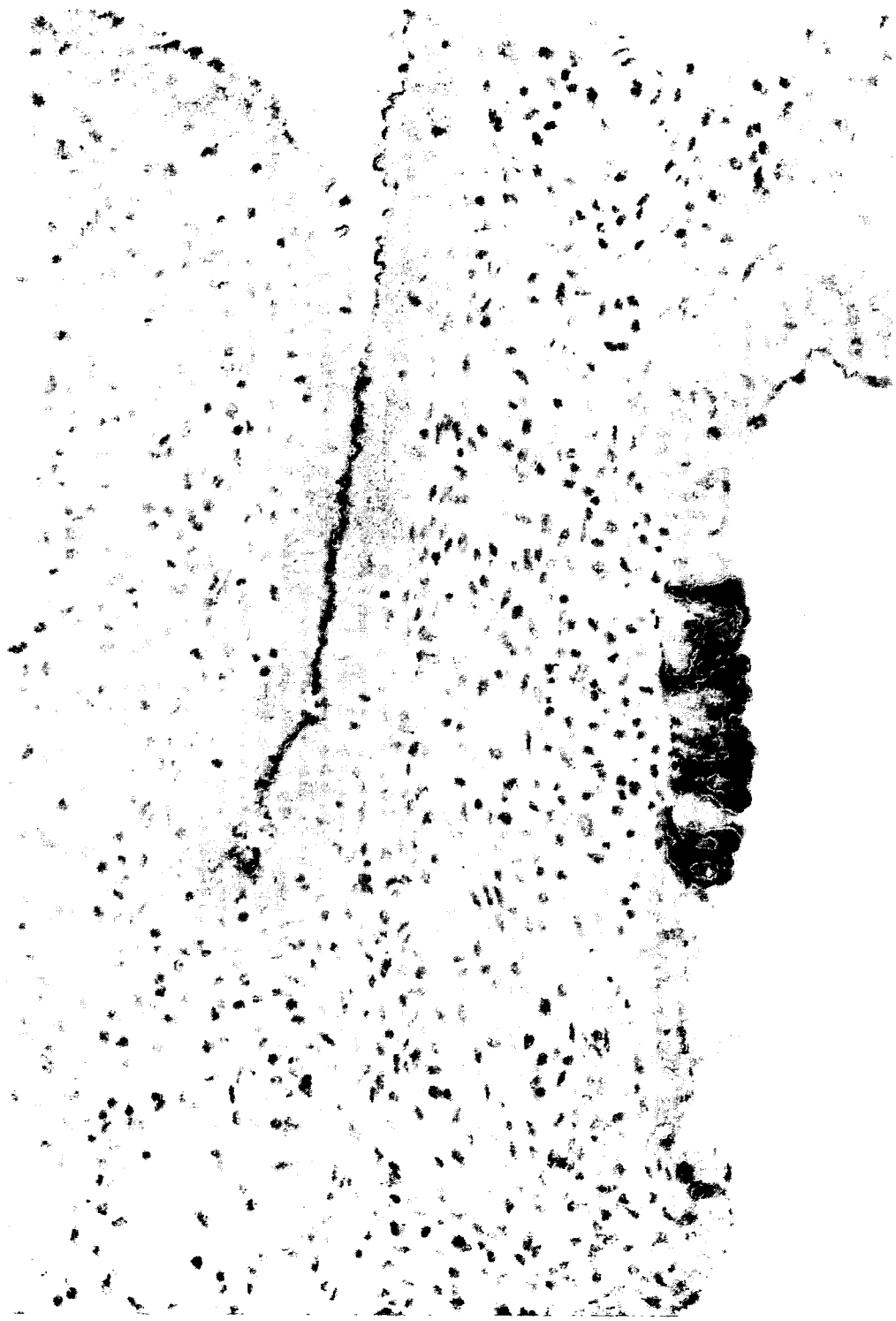
FIG. 8. Immunohistochemical staining of hK10 in fallopian tube (formalin-fixed paraffin-embedded tissue). There is positivity (grey color) on the luminal surface of the epithelial lining cells of the fallopian tube with focal intense positivity within the cytoplasm of some of the cells (original magnification ×400).

The distribution of hK10 in various human tissue extracts and biological fluids were investigated with the developed hK10 immunoassay. As FIG. 7 shows, hK10 is present in many tissues, such as salivary gland, skin, colon, fallopian tube, prostate, testis, pituitary, endometrium, and lung. hK10 is also detectable in various biological fluids, including milk, seminal plasma, serum, cerebrospinal fluid, and amniotic fluid (Table 1). hK10 was immunohistochemically localized in the epithelial cells of fallopian tube, as shown in FIG. 8. hK10 is present in the cytoplasm of epithelial cells lining the lumen.

Recovery of hK10 in Various Biological Fluids

These data (Table 2) indicate that, with the exception of CSF (recovery 88-100%), recovery is incomplete and ranges from 50-80% in serum, 0 to 77% in milk 64-100% in seminal plasma and 18-53% in amniotic fluid.

Figure 9:
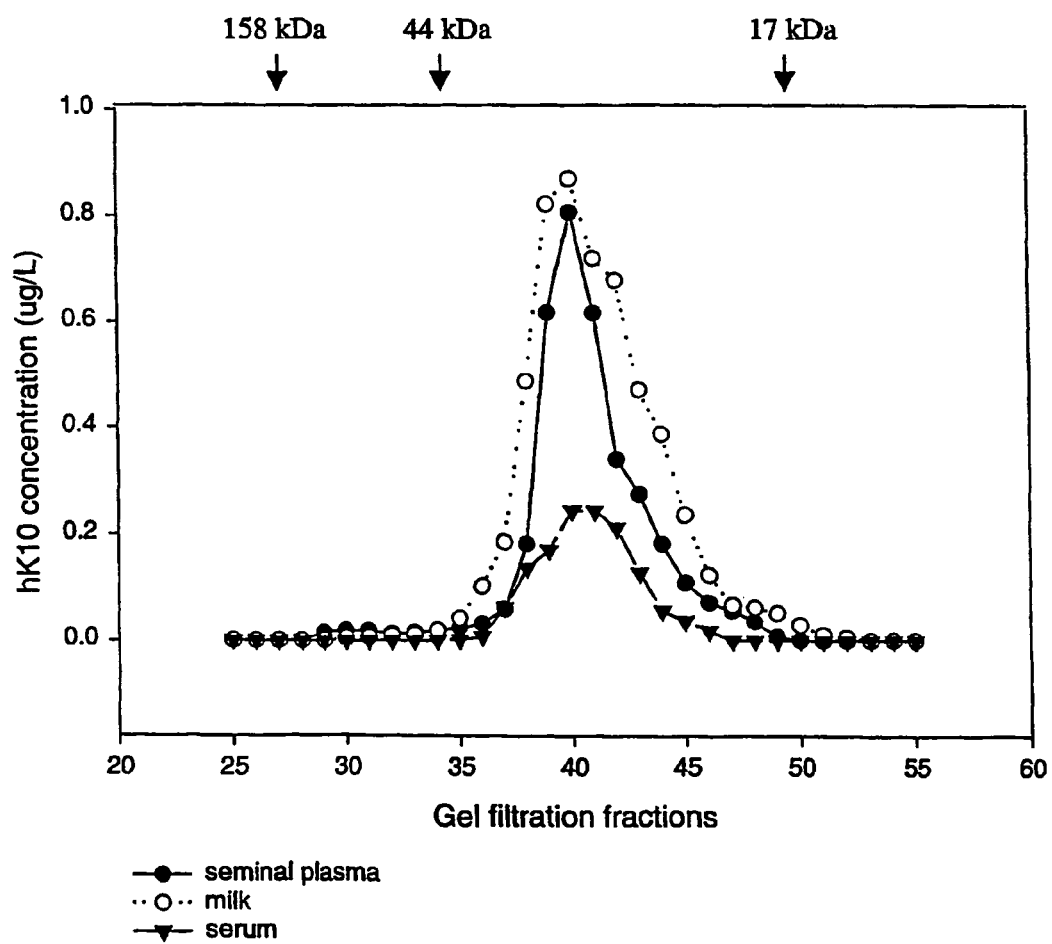
FIG. 9. Fractionation of milk, seminal plasma, and serum with size-exclusion high performance liquid chromatography. The presence of hK10 in different fractions was measured with hK10 immunoassay. A single peak (fraction 40) was detected in all three samples. Molecular mass standards were also separated on the same column and their corresponding fractions are shown on top of the graph. The immunoreactive peak elutes at around 30 kDa in all three clinical samples.

Fractionation of Biological Fluids with Size-Exclusion High Performance Liquid Chromatography In order to investigate the molecular mass of the protein that is detected in the biological fluids, three samples were fractionated with gel filtration, including milk seminal plasma, and serum. The presence of hK10 in various fractions was measured with the developed immunoassay. When the fluorescence counts were plotted against the different fractions, a single peak (fraction 40), which corresponds to about 30 kDa, is detected (FIG. 9). No higher molecular mass complexes were found. These results indicate that the protein detected with the hK10 immunoassay is a single species, with a molecular weight of 30 kDa, which is consistent with the molecular mass of free hK10.

Discussion

The human kallikrein 10 (KLK10) gene was initially named as the normal epithelial cell-specific 1 gene (NES1) and was cloned by subtractive hybridization between a tumorigenic and a non-tumorigenic breast cell line (Liu X L, Wazer D E, Watanbe K and Band V., Cancer Res 1996; 56:3371-9.). The genomic organization of this gene was recently determined and it was mapped to the same chromosomal locus as other human kallikreins (Luo L, Herbrick J A, Scherer S W, Beatty B, Squire J and Diamandis E P., Biochem Biophys Res Commun 1998; 247:580-6). Based on these data, and a number of other similarities between NES1 and other human kallikreins (reviewed in Diamandis E P, Yousef G M, Luo L, Magklara I and Obiezu C V., Trends Endocrinol Metab 2000; 11:54-60), this gene is classified as a new member of the human kallikrein gene family. Recently, uniform nomenclature for the expanded human kallikrein gene family has been developed and NES1 was renamed as KLK10 (Diamandis E P, et al, Clin Chem, 2000).

Although hK10 was predicted to be a secreted protein (Liu X L, Wazer D E, Watanabe K and Band V., 1996; 56:3371-9), no methods currently exist for detecting the protein with high sensitivity and specificity. Thus the task of developing such a method was understaken, based on non-competitive immunoassay principles. For detection, time-resolved fluorometry was used to achieve high sensitivity (Christopoulos T K and Diamandis E P., Anal Chem 1992; 64:342-6). Since there is no known natural source of large amounts of hK10, it was expressed it in *Pichia pastoris*. The protein was then purified to homogeneity by combining ion-exchange and revered-phase chromatography. This technology ensures complete absence of homologous proteins and other contaminants in the final preparation. The recombinant hK10 protein was positively identified using mass spectrometry. It appears that the protein is slightly shorter than native hK10, likely due to differences in glycosylation.

The developed assay is highly sensitive, detecting hK10 at levels of 0.05 µg/L or higher. Furthermore, this assay appears to be very specific since no detectable cross-reactivities were demonstrated with the highly homologous kallikrein proteins PSA (hK3), hK2 and hK6. Also, substitution of the antibodies with preimmune serum from the same animals completely abolished the signal. Size exclusion high performance liquid chromatography has further indicated that the three biological fluids tested (serum, milk, seminal plasma), contain only one immunoreactive peak of the expected molecular weight (~30 kDa). These data further suggest that the immunoassay detects the free fraction of hK10 in these biological fluids. The possibility that hK10 may be partially complexed to protease inhibitors, like PSA, could not be excluded (Stenman U H, et al, Cancer Res 1991; 51:222-6; Lijia H et al, Clin Chem 1991; 37:1618-27; Zang W M, et al.; Clin Chem 1998; 44:2471-9; and Zhou A, et al., Clin Chem 1993; 39:2483-91).

hK10 was detected in various tissue but predominantly in salivary glands, skin and colon. Relatively high levels of hK10 were identified in many biological fluids, including milk of lactating women, seminal plasma, amniotic fluid, male and female serum and cerebrospinal fluid (Table 1). Since hK10 is a secreted protein, the concentration of this biomarker in serum may change during initiation and progression of various diseases, including cancer. Currently, there is no literature report associating expression of hK10 with any human disease with the exception of KLK10 downregulation in breast cancer cell lines (Liu X L, et al, Cancer Res 1996; 56:3371-9) and an abstract which describes downregulation of KLK10 mRNA in aggressive forms of prostate cancer (Luo L Y and Diamandis E P., Clin Biochem 2000; 33:237. [Abstract]).

Immunohistochemical localization of hK10 in the fallopian tube has indicated that this antigen is produced by the luminal epithelial cells lining the fallopian tube. The immunoreactivity was detected in the cytoplasm and lumen, further suggesting that this protease is secured. Furthermore, the presence of high levels of hK10 in milk, seminal plasma, amniotic fluid and spinal fluid suggests that this protein is actively secreted by epithelial cells of breast, male reproductive organs, the fetoplacental unit and brain cells.

The recovery of hK10 from the biological fluids tested (Table 2) is incomplete, with the exception of CSF. In serum, recovery ranges from 50-82%, a situation similar to the recovery of PSA (Yu H and Diamandis B P, Clin Chem 1993; 39:2108-14). In seminal plasma the recovery ranges from 64-100%. Lowest recovery was seen with milk and amniotic fluid. The low recovery is either due to sequestration of hK10 by proteinase inhibitors (e.g. $\alpha_2$-macroglobulin) as it happens with PSA or to uptake of hK10 in lipids present in milk and amniotic fluid.

In conclusion, a highly sensitive and specific immunofluorometric assay for measuring hK10 in biological fluids and tissue extracts is described.

Example 2

Materials and Methods

Serum Samples

The serum samples used in this study were leftovers of routine testing from patients with various malignancies. In order to increase the possibility of detecting hK10 alterations in serum, patients included in this study had relatively high tumor burden (as indicated by tumor marker level at least 10-fold higher than the upper limit of normal). All serum samples were stored in −20° C. until analysis for a maximum time of one year. The procedures were in accordance with the Ethical standards of the Helsinki Declaration of 1975, as revised in 1983 and have been approved by the Institutional Review Boards.

Analysis of Tumor Markers

The tumor marker markers CA125, PSA, CEA and AFP were analyzed on the Elecsys immunoassay analyzer (Roche Diagnostics, Indianapolis, Ind.). CA15.3, CA19.9 and hCG were analyzed on the Immuno 1 immunoassay analyzer (Bayer Diagnostics, Tarrytown, N.Y.) and calcitonin was measured with a radioimmunoassay kit from Diasorin, Italy. The upper limit of normal values for these tumor markers were 35 KU/L (CA125), 4 μg/L (PSA), 10 μg/L (AFP), 5 μg/L (CEA), 35 KU/L (CA15.3). 37 KU/L (CA19.9), 10 IU/L (hCG) and 100 ng/L (calcitonin).

Immunofluorometric Assay for hK10

The hK10 immunoassay utilizes two hK10-specific polyclonal antibodies, one raised in mouse and the other raised in rabbit. The details of this assay are described in Example 1. In brief, mouse anti-hK10 antiserum was captured with sheep anti-mouse IgG antibody (Jackson Immunoresearch West Grove, Pa.) immobilized on 96-well white polystyrene microtiter plates. 50 L of serum samples (without pretreatment) were then added into each well followed by incubation and washing. Rabbit anti-hK10 antiserum was subsequently applied, incubated and washed. Finally, alkaline phosphatase-conjugated goat anti-rabbit IgG (Jackson Immunoresearch) was added, incubated and washed. To detect the signal, time-resolved fluorometry was used, essentially as described elsewhere (18). The measurement range of this assay is 0.05-20 μg/L with a precision of less than 10%.

Results

Figure 10:
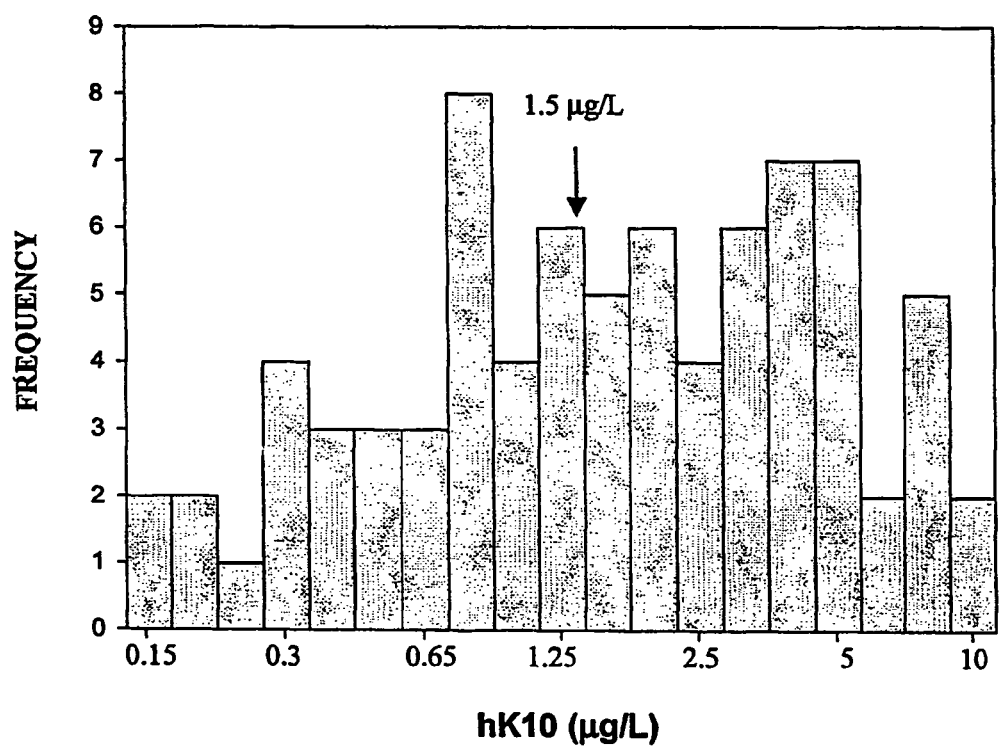
FIG. 10: Frequency distribution of hK10 concentrations in the serum of 80 patients with ovarian cancer. The level of 15 µg/L, used as a cutoff in Table 3, is indicated by an arrow. About 57% of ovarian cancer patients have serum hK10 higher than this cutoff value.

A total of 374 serum samples were analyzed from either normal individuals or patients with various malignancies, with a recently described sensitive and specific hK10 immunoassay. The results are shown in Table 3. The majority (56%) of the ovarian cancer patients had serum hK10 levels higher than 1.5 μg/L (an arbitrarily selected cutoff). However, none of the normal controls, breast cancer, medullary thyroid carcinoma, and prostate cancer patients had serum hK10 higher than this value. The other malignancies screened only had a small proportion of patients with serum hK10 levels higher than this cutoff, including gastrointestinal cancer (15%), lung cancer (13%), and testicular cancer (2%). When the cutoff value was 0.8 μg/L (the $100^{th}$ percentile of normal males and females), the positivity rate for ovarian cancer was elevated to 78%, but significant numbers of patients from other malignancies were also positive, as shown in Table 3. The distribution of hK10 in serum of ovarian cancer patients is shown in FIG. 10.

Figure 11:
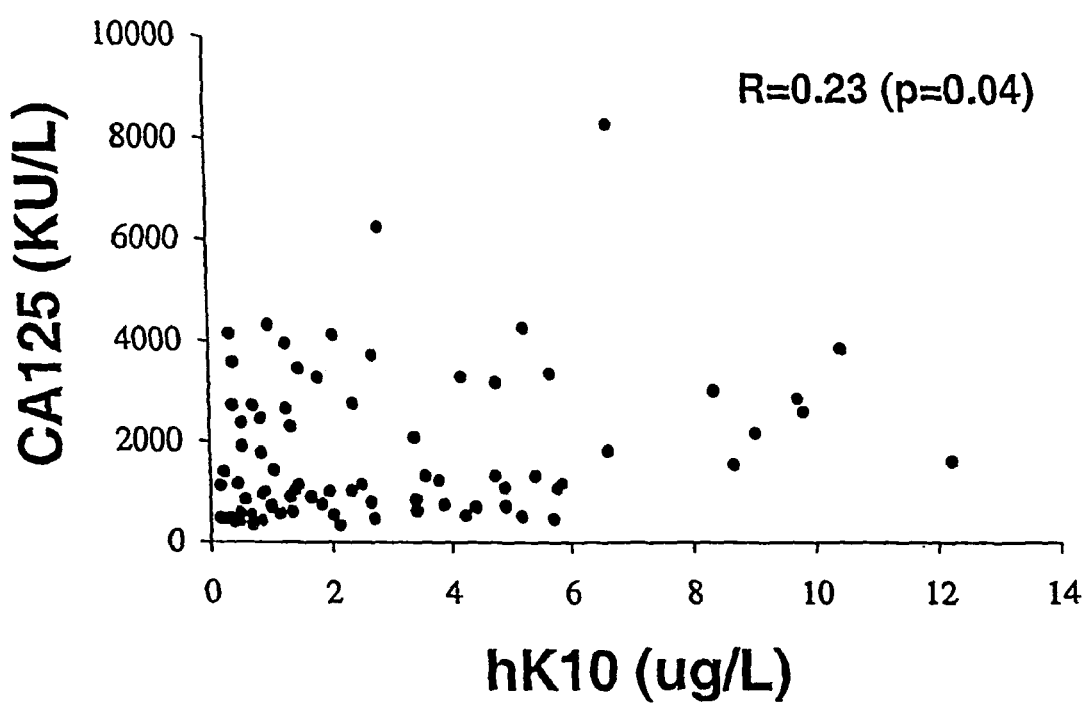
FIG. 11: Correlation between CA 125 and hK10 concentration in 79 serum samples from ovarian cancer patients. Pearson correlation coefficient R=0.23.

To investigate the correlation between hK10 and CA125 in serum of ovarian cancer patients, linear regression was performed. As FIG. 11 shows, there is a weak correlation between serum hK10 and CA125 in ovarian cancer patients (r=0.23, p=0.04).

Figure 12:
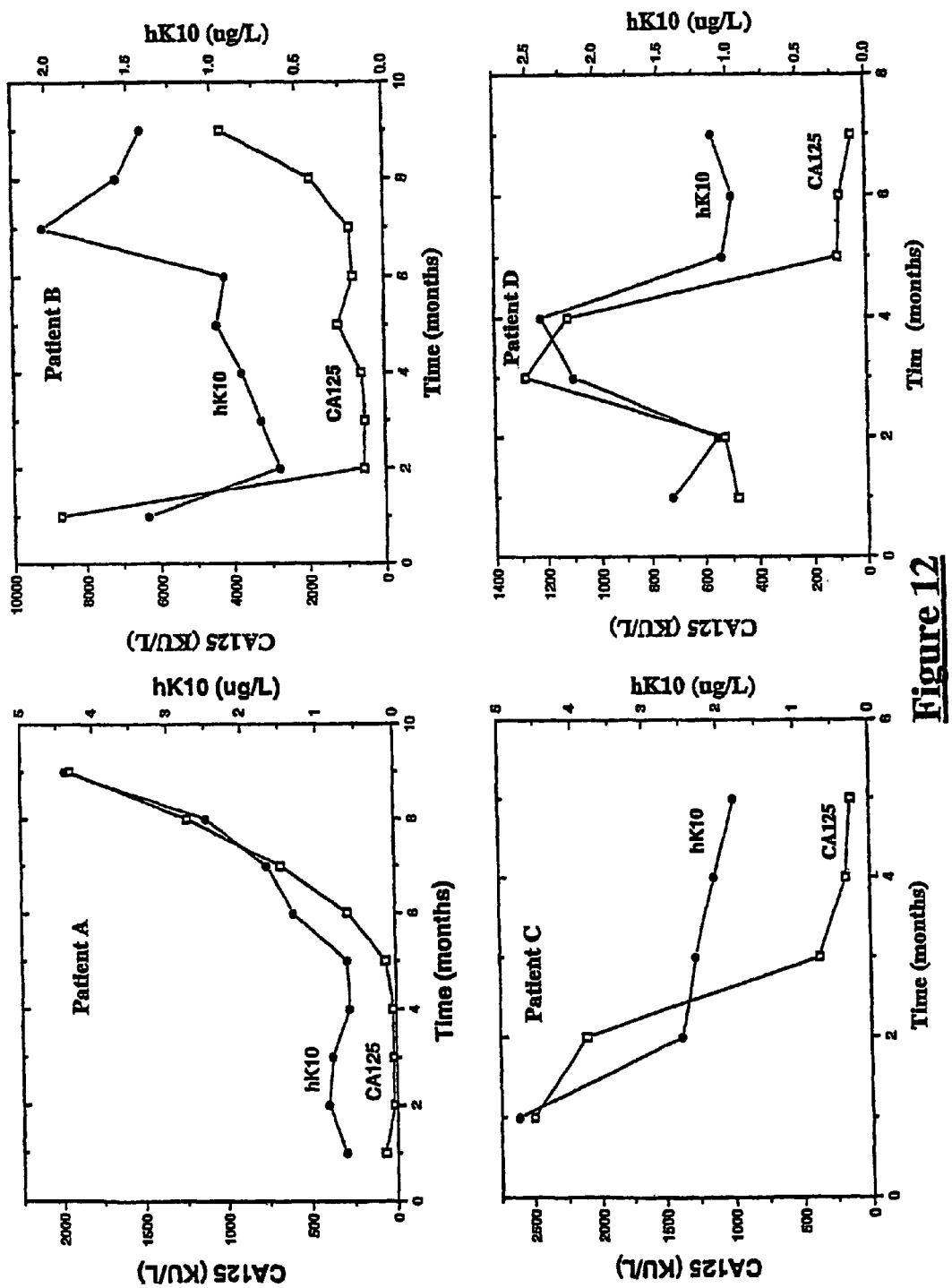
FIG. 12: Analysis of hK10 and CA125 in serial serum samples from ovarian cancer patients, who were monitored post-primary treatment.

In order to further investigate whether hK10 serum concentration has any value for patient monitoring, serial serum samples from four ovarian cancer patients were also analyzed, along with CA125. As shown in FIG. 12, serum hK10 concentration changes in parallel to CA125 in most cases. These data suggest that hK10 may have potential for ovarian cancer monitoring after primary treatment.

Discussion

In this study, 374 serum samples were analyzed from normal individuals and patients with various malignancies. Serum hK10 concentration was significantly elevated (higher than 1.5 μg/L) in the majority of ovarian cancer patients, but not in serum of normal individuals or patients with other types of cancer (Table 3). This elevation correlates weakly with CA125 (FIG. 11). Also, hK10 serum concentration fluctuates according to the tumor burden, as assessed by analysis of CA125 (FIG. 12). These results indicate that hK10 may constitute a new serological marker for ovarian cancer.

The results suggest that hK10 may have value as a potential ovarian cancer biomarker. hK10 was elevated in a majority of ovarian cancer patients. The specificity can be manipulated by selecting an appropriate cutoff, as shown in Table 3. However, positive samples were found from patients with other malignancies, including those from gastrointestinal, lung, prostate, thyroid, testicular and breast cancer. This shortcoming is known for many other cancer biomarker (23). hK10 does not correlate well with CA125, which indicates that it may be used in conjunction with CA125 to achieve more sensitive and specific ovarian cancer detection. Further, hK10 changes with tumor burden, suggesting that it may also be useful for disease monitoring. The samples used in this study have relatively high CA125 values (at least 10 times higher than the upper reference value).

This represents the first evidence that serum hK10 significantly increases in the majority of ovarian cancer patients and in a smaller proportion of other cancers. hK10 may constitute a new serological biomarker for ovarian cancer diagnosis and monitoring.

Example 3

KLK10 Human Ovarian Tissue

Methods

Ovarian Cancer Patients. One hundred eighty-two patients with primary ovarian cancer were included in this study. These patients under surgery for ovarian cancer at the Department of Gynecology, University of Turin, Italy. Ages of these patients ranged from 25 to 82 with a median of 59 years. Clinical and pathological information were documented at the time of surgery, including stage, grade, histologic types, residual tumor, debulking success, menopausal status and response to chemotherapy. The staging of the tumors was according to the International Federation of Gynecology and Obstetrics (FIGO) criteria. The classification of the histologic type was based on the World Health Organization and FIGO recommendations. Most of the tumors (81) included in this study were of serous papillary histologic type, whereas the remaining tumors were endometrioid (30), undifferentiated (27), mucinous (11), clear cell (13), mullerian (12), sarcoma (2), other non-epithelial (4) and unknown (2). The size of the residual tumors ranged from 0 to 9 cm, with a median of 1.0 cm.

Follow-up information (median follow-up period of 62 months) includes survival status (alive or deceased) and disease status (disease-free or recurrence), and was available for 163 patients. Among these patients, 58 died and 85 relapsed.

Preparation of the Cytosolic Extracts. Tumor tissues were frozen in liquid nitrogen immediately after surgery and stored at −80° C. until exaction. 200 mg of frozen tissue was first pulverized on dry ice to a fine powder. One ml of extraction buffer (50 mM Tris, pH 8.0, 150 mM NaCl, 5 mM EDTA, 10 g/L of NP-40 surfactant, 1 mM phenylmethyl sulphonyl fluoride, 1 g/L of aprotinin, 1 g/L of leupeptin) was then added to the tissue powders and incubated on ice for 30 minutes with repeated shaking and vortexing every ten minutes. Finally, the mixtures were centrifuged at 14,000 rpm at 4° C. for 30 minutes and the supers (cytosolic extracts) were collected. All tissue cytosolic extracts were stored at −80° C. until they were analyzed. Protein concentration of the cytosolic extracts was determined with the bicinchoninic acid method, with albumin as standard (Pierce Chemical Co., Rockford, Ill.).

Measurement of hK10 in Ovarian Cytosolic Extracts. The concentration of hK10 in the cytosolic extracts was quantified with a highly sensitive and specific non-competitive immunoassay for hK10. This assay was described and evaluated in detail in Examples 1 and 2. The assay in at both mouse and rabbit anti-hK10 antiserum. In brief, mouse anti-hK10 polyclonal antiserum was captured with sheep anti-mouse IgG, Fc fragment specific antibody (Jackson Immunoresearch, West Grove, Pa.) on 96-well polystyrene microtiter plates. 25 µL of cytosolic extracts and 100 µL of BSA (60 g/L) were then added into each well, incubated for one hour with gentle shaking, and washed. Rabbit anti-hK10 polyclonal ante was subsequently applied, incubated and washed. Finally, alkaline phosphatase-conjugated goat anti-rabbit IgG (Jackson Immunoresearch) was added, incubated, and washed as before. To detect the signal, time-resolved fluorometry was used. The detection range of this assay is 0.05-20 µg/L. An tumor extracts were measured in duplicate and hK10 concentrations in µg/L were converted to ng of hK10 per mg of total protein to adjust for the amount of tumor tissue extracted.

Localization of hK10 in Ovarian Tumor Specimens by Immunohistochemistry. A rabbit polyclonal antibody was raised against hK10 full-size recombinant protein, produced in yeast cells. Immunohistochemical staining for hK10 was performed according to a standard immunoperoxidase method. Briefly, paraffin-embedded tissue sections (4 µm) were fixed and dewaxed. Endogenous peroxidase activity was blocked with 3% aqueous hydrogen peroxide for 15 minutes. Sections were then treated with 0.4% pepsin at pH 2.0 for 5 minutes at 42° C. and blocked with 20% protein blocker (Signet Labs) for 10 minutes. The primary antibody was then added at 1:400 dilution for 1 hour at room temperature. After washing, biotinylated secondary antibody (Signet), diluted 4-fold in antibody dilution buffer (DAKO) was added. The streptavidin horseradish peroxidase complex was then added for 30 minutes at room flare. Detection was achieved with amino ethyl carbazole (AEC) for 5-10 minutes. After counterstaining with hematoxylin, the slides were mounted with cover slips.

Statistical Analysts. Statistical analysis was performed with SPSS software (SPSS Inc. Richmond, Calif.). To analyze data, patients were divided into different groups according to clinical and pathological parameters. Because the distribution of hK10 protein concentration in the ovarian tumor cytosolic was not Gaussian, the differences between groups were determined by the nonparametric Mann-Whitney U test and the analysis of differences among more than two groups were performed with the Kruskal-Wallis test in which hK10 was considered as a continuous variable. hK10 values were also classified into two categories (hK10-positive and hK10-negative groups) and their relationships to various clinicopathological variables were analyzed with the $\chi^2$ test and the Fisher's exact test (where applicable). The impact of hK10 on patient survival (progression-free and overall survival) was assessed with the hazards ratio (a relative risk for relapse or death) that was calculated with the univariate and multivariate Cox proportional hazards regression model (28). In the multivariate analysis, the clinical and pathological variables that may affect survival, including stage of disease, tumor grade, residual tumor, histologic type and age were adjusted. Kaplan-Meier progression-free survival and overall survival curves (29) were constructed to demonstrate the survival differences between the hK10-positive and hK10-negative patients. The log rank test (30) was used to examine the significance of the differences among the survival curves. Furthermore, the patients were divided into different subgroups based on disease stage, tumor grade, and debulking success. The survival analysis was then repeated separately for each subgroup of patients.

Results

Figure 13:
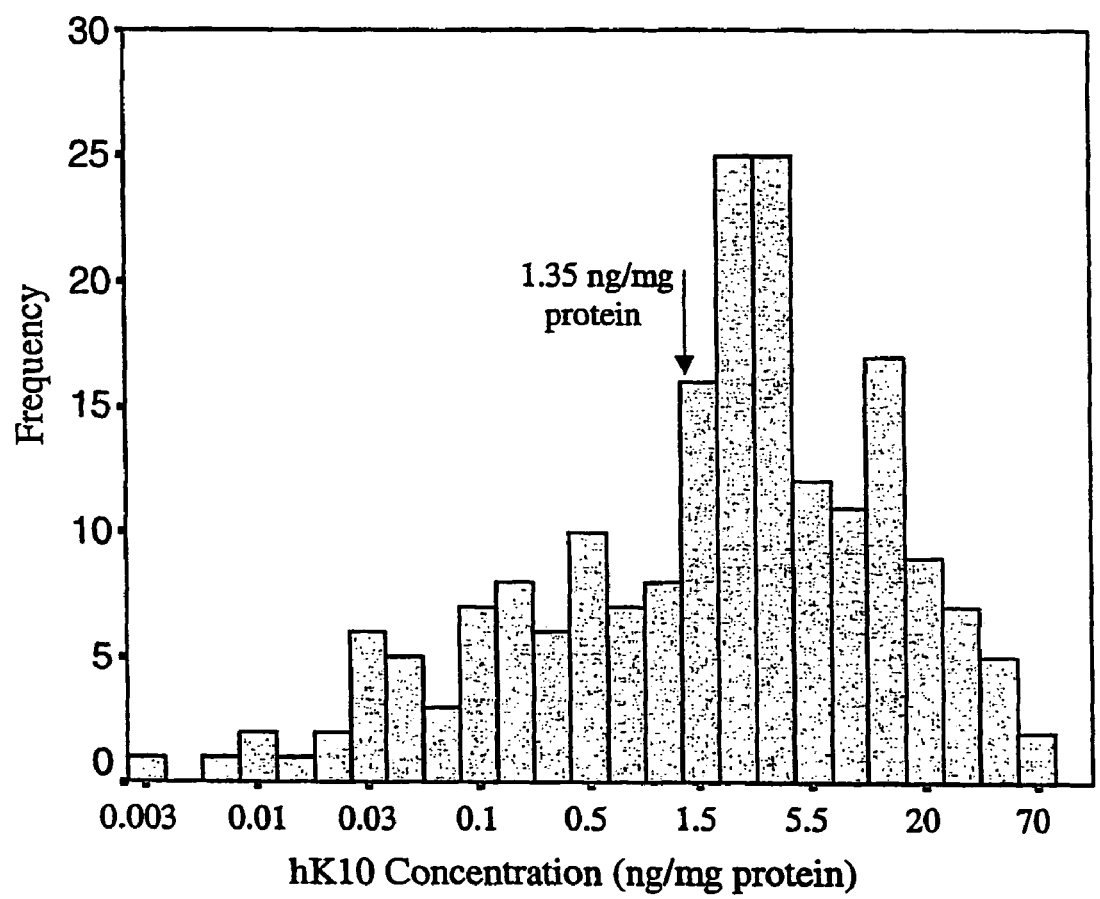
FIG. 13 is a graph showing the frequency distinction of hK10 concentration in ovarian tumor cytosols. The optimal cutoff value, 1.35 ng/mg of total protein ($33^{rd}$ percentile), was used to classify tumors as hK10-high and hK10-low.
Figure 14:
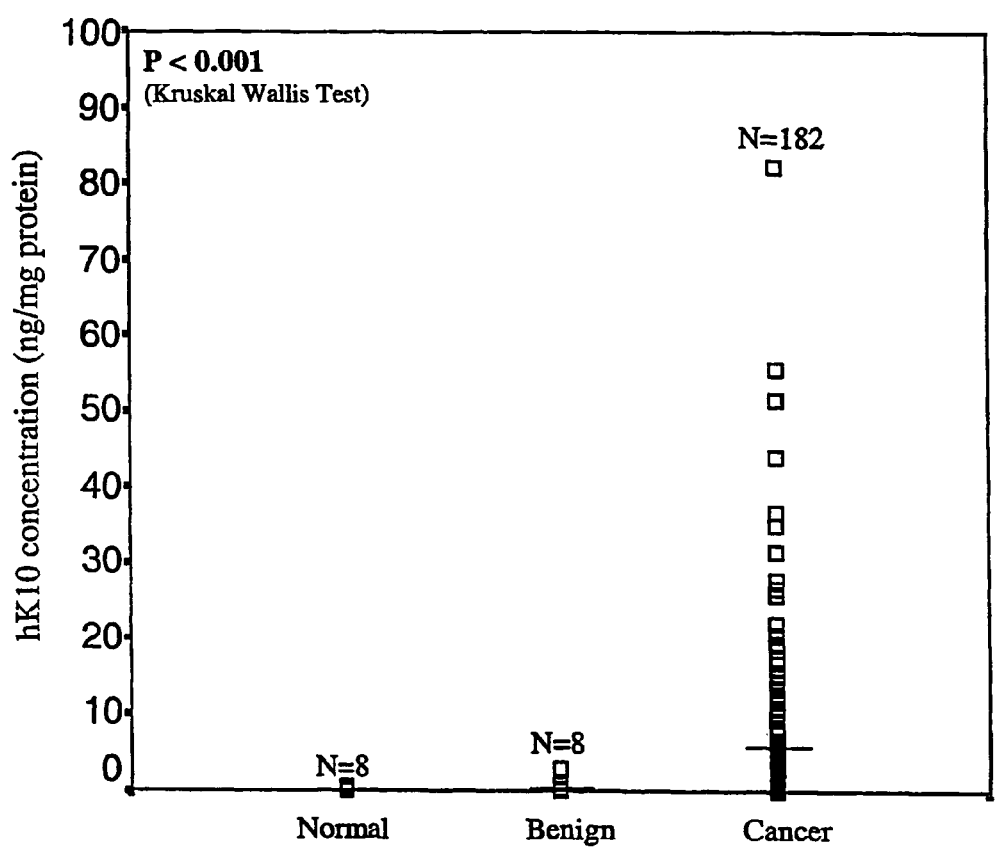
FIG. 14 is a graph showing a comparison of hK10 concentration in extra from normal ovarian tissues (Normal), ovarian tissues with benign disease (Benign), ovarian cancer (Cancer). Numbers of patients in each group (N) measured are indicated. Horizontal bars, mean hK10 concentration. Kruskal-Wallis test showed hK10 concentration was significantly elevated in the ovarian tumor cytosols (P<0.001).

Distribution of hK10 Concentration in Ovarian Tumor Cytosols hK10 concentration in ovarian tumor cytosolic from 182 patients ranged from 0 to 84 ng/mg of total protein. The mean was 7.1 ng/mg, with a median of 2.6 ng/mg. The frequency distribution curve is shown in FIG. 13. hK10 concentration was highly elevated in ovarian tumor cytosols, compared to the cytosols prepared from normal ovarian tissues or tissue with benign ovarian disease (FIG. 14). The mean, standard error and range of values, were as follows: normal ovarian tissues, 0.27±0.06, 0-0.62; benign ovarian disease, 0.61±0.33, 0-0.3; ovarian cancer, 7.1±0.7, 0-84. The optimal hK10 cutoff value for further analyses, was selected by the $\chi^2$ test, based on the ability of this value to predict the overall survival of the study population. A value of 13.5 ng/mg of total protein was found to be the optimal cutoff ($\chi^2$=6.3, P=0.012) and represents the 33$^{rd}$ percentile. Tumors were then dichotomously categorized as hK10-high and hK10-low (FIG. 13).

Figure 15:
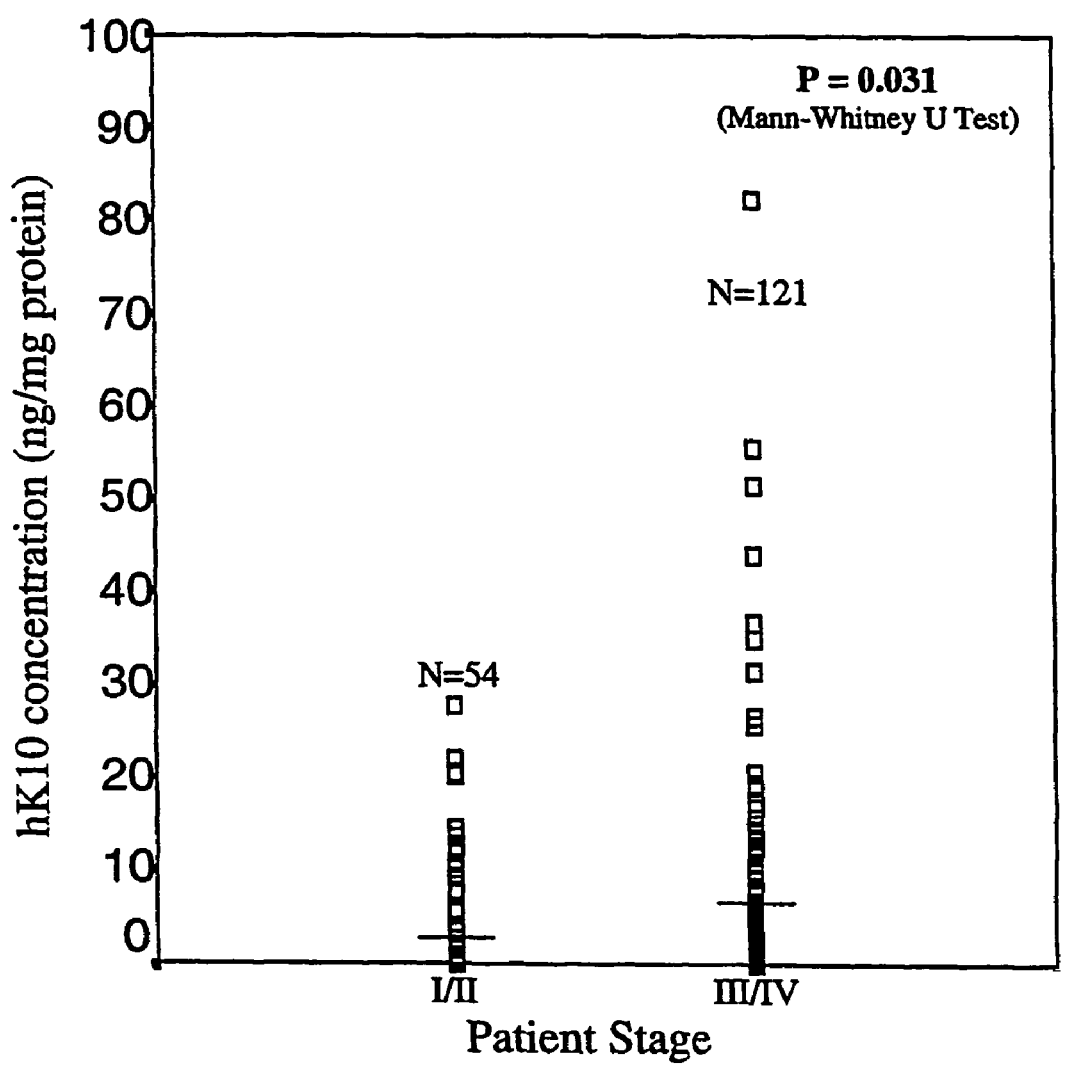
FIG. 15 is a graph showing the distribution of hK10 concentration in extracts from stage I/II and stage III/IV ovarian cancer patients. Patient number in each group (N) is shown. Horizontal bars, mean value of hK10 concentration. Mann-Whitney test indicated hK10 concentration was significantly elevated in patients with stage III/IV ovarian cancer (P<0.05).

Relationships between hK10 Status and Other Clinicopathological Variables. The distributions of various clinicopathological variables among hK10-high and hK10-low patients are summarized in Table 4. The relationships between hK10 and these variables were examined with $\chi^2$ test and Fisher's exact test. No relationship was observed between hK10 status and tumor grade, menopause status, and response to chemotherapy. However, hK10-high patients more frequently had advanced disease stage (stage II-IV), serous histologic type, larger residual tumor (>1 cm), and suboptimal debunking (all P<0.05). With Mann-Whitney U test, it was also demonstrated that hK10 concentration was significantly higher in cytosols from stage III-IV ovarian cancer than those from stage I/II, indicating that high hK10 concentration is associated with advanced disease stage (FIG. 15).

Figure 16:
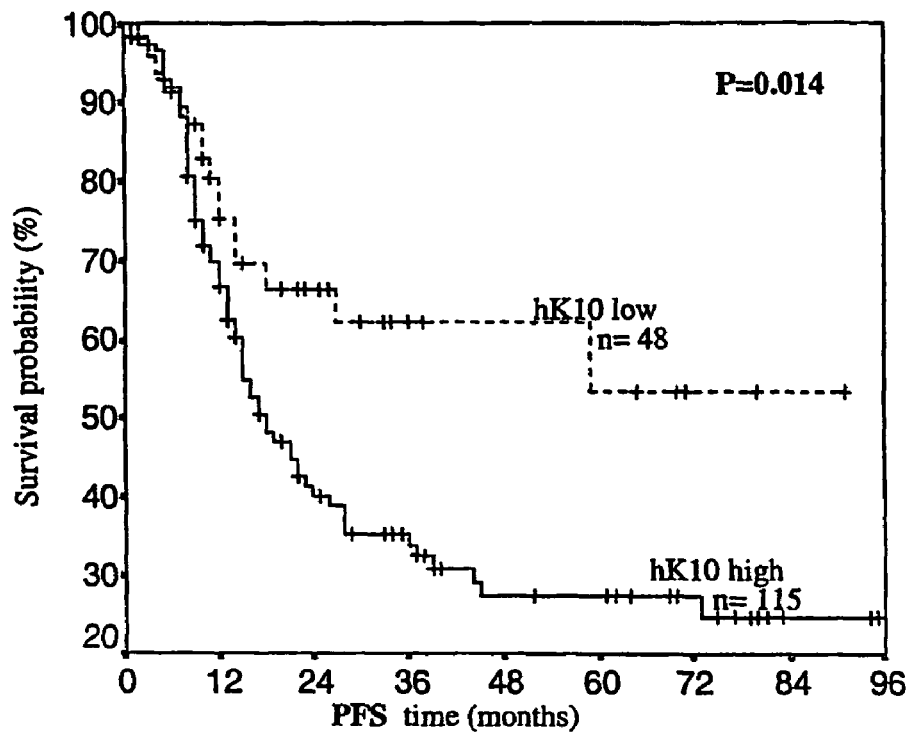
FIG. 16 are Kaplan-Meier survival curves. Top, PFS; Bottom, OS. The patient number in each group (n) and Ps are indicated. The lower PFS and OS rates in hK10-high are statistically significant.
Figure 16:
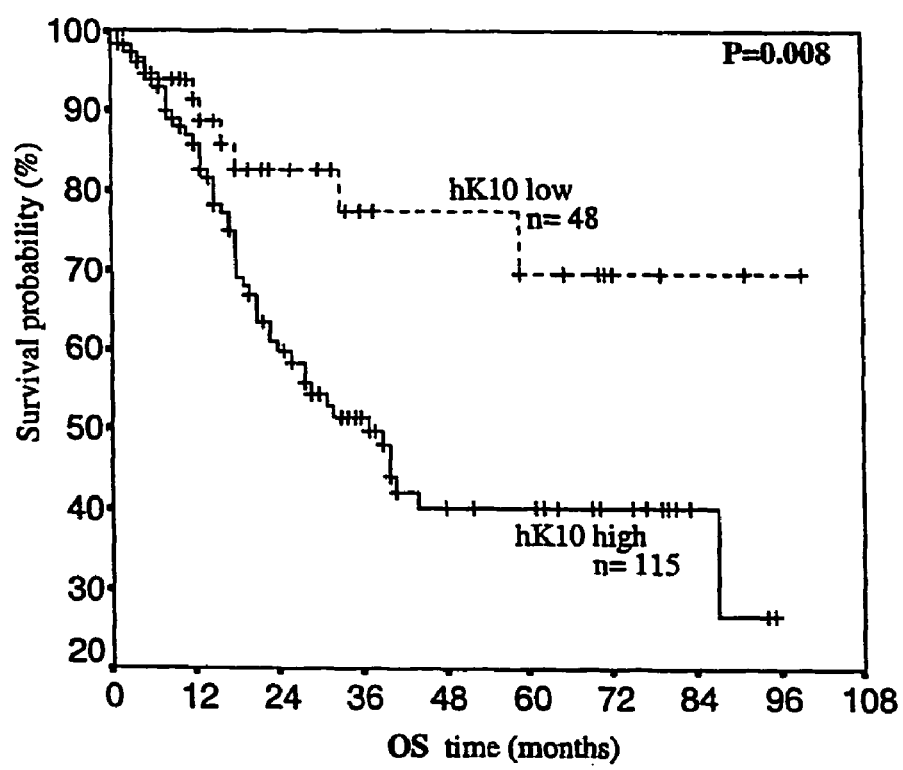

Univariate and Multivariate Survival Analysis. The results of survival analysis are presented in Table 5. In univariate analysis, hK10-high patients had significantly increased risk for relapse (hazards ratio, HR=1.93) and death (HR=2.42) (P<0.05). When hK10 was considered as a continuous variable, a similar result was also observed. Kaplan-Meier survival curves demonstrated survival differences between hK10-high and hK10-low patients. As FIG. 16 shows, the probabilities for progression-free and overall survival are lower in hK10-high patients than in hK10-low patients. In multivariate analysis, progression free and overall survival in hK10-high patients were no different from the survival rates of hK10-low patients (Table 5). Stage of disease, grade, and residual tumor size were identified to have prognostic significance m univariate analysis, however, in multivariate analysis, only stage and residual tumor remained significant.

Figure 17:
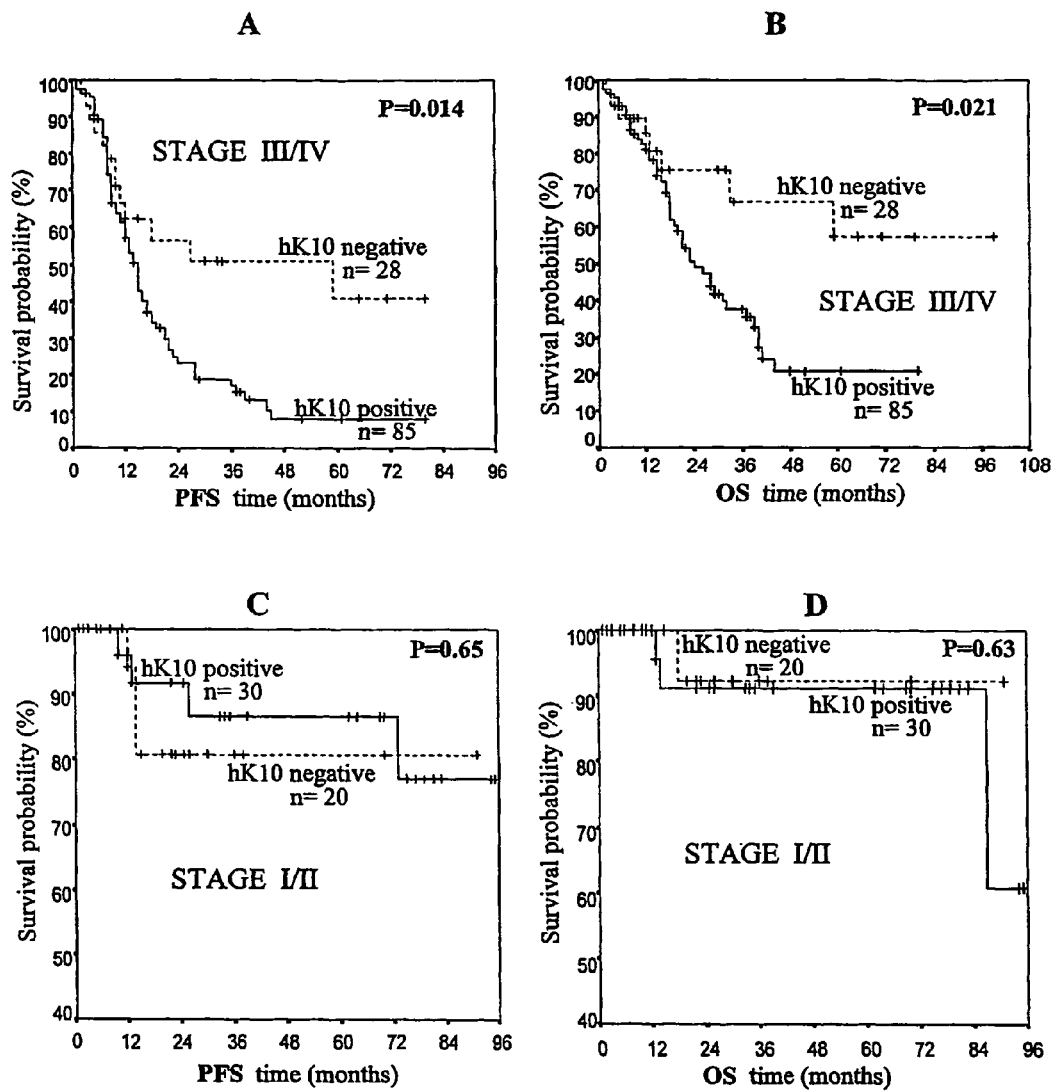
FIG. 17 are graphs showing PFS and OS of patients with hK10-high and hK10-low ovarian tumors stratified by the tumor stage. The patient number in each group (n) and Ps are indicated. Among patients with stage III/IV disease, hK10-high was associated with lower PFS and OS rates. This association was not observed in patients with stage I/II disease.

Univariate and Multivariate Survival Analysis in Subgroups of Patients. The patients were divided into different subgroups based on disease stage, tumor grade, and debulking success. Univariate and multivariate survival analyses were then performed. The results are shown in Table 6. Univariate analysis has shown that among patients who have stage III/IV disease, hK10-high patients are about 2-fold more likely to relapse and die than hK10-low patients. This survival difference remained significant even after the data were subjected to multivariate analysis. However, this was not observed among patients who have stage I-II disease. hK10 status has no effect on relapse and survival between subgroups of patients who have different tumor grade or debulking success. When Kaplan-Meier survival curves were constructed, they showed similar results (FIG. 17).

Figure 18:
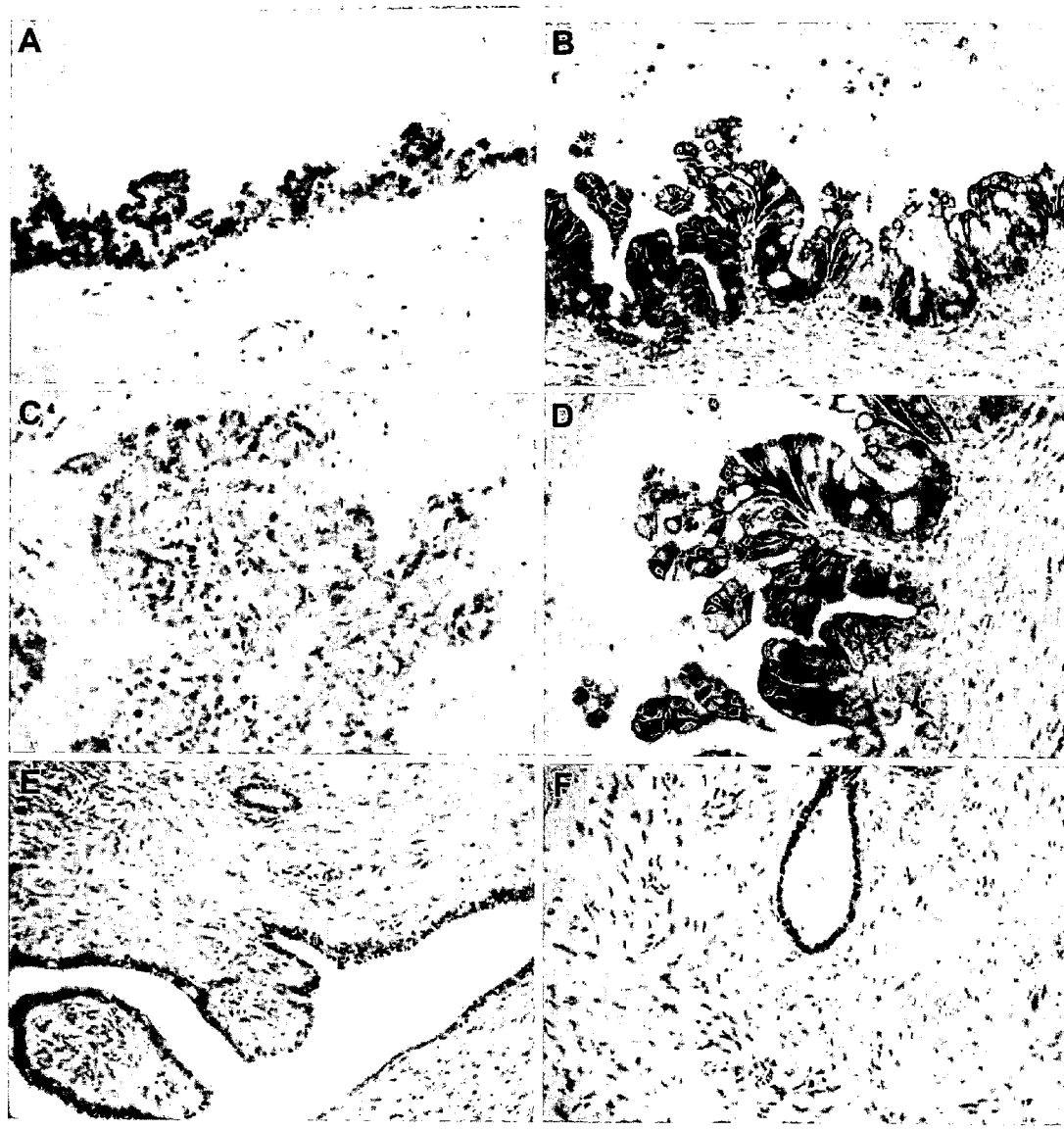
FIG. 18 are blots showing immunohistochemical localization of hK10 in ovarian tumor tissues. A and C, intracytoplasmic staining in epithelial cells in papillary lining (A) and invasive component of an invasive papillary serous carcinoma (×400). B and D, intracytoplasmic staining in epithelial cells of a borderline mucinous tumor (×400). E and F, intracytoplasmic staining in epithelial component of a serous cystadenofibroma (E) and in both epithelial and stromal cells (F) of the same tumor (×400).

Immunohistochemical Localization of hK10 in Ovarian Tumors. In FIG. 18 the immunohistochemical localization of hK10 protein in a few representative specimens from ovarian cancer patients is presented Discussion In this study, hK10 protein was found to be expressed in the epithelial cells of the ovary and its expression was dramatically elevated in cancerous vs normal tissues. This elevation was more strongly associated with late disease stage, serous histologic type, suboptimal debulking, and large residual tumor. For patients who have stage III-IV ovarian cancer, hK10 overexpression is an independent prognostic indicator which correlates with poor progression free and overall survival.

Ovarian cancer is the most lethal gynecological malignancy (31). This is due to the fact that at early stage, this disease is occult and a symptomatic. By the time diagnosis is made, more than half of the patients have stage III-IV disease. Furthermore, this disease has a tendency to relapse (32). Some improvement in the overall survival has been observed in the past decade due to better therapeutic strategies (33). The clinical outcome of ovarian cancer varies from patient to patient. Biomarkers that can predict disease outcome, could help tailor different therapeutic strategies to meet individual needs. The results indicate that hK10 is one such prognostic biomarker. Combined with other prognostic indicators, this new biomarker may contribute to patient subclassification, for the purpose of individualizing more effective treatments to such subgroups.

Advanced disease stage, serous histologic type, and large residual tumor are known indicators for aggressiveness and poor outcome in ovarian cancer (34). In this study, the same association was observed (Table 5), and it was shown that hK10 expression correlates with these clinicopathological features. The biological rationale underlying the overexpression of hK10 and its association with aggressiveness in ovarian cancer may be explained as follows. It is known that the aggressiveness of a tumor largely depends on its ability to invade adjacent tissues and to metastasize to distant sites. During the process of cancer invasion and migration, natural barriers such as interstitial connective tissues and basement membranes have to be degraded. Proteases are widely believed to be involved in these processes (35, 36). Therefore, the amount of proteases released by the primary tumor may reflect the ability of a tumor to spread. Overexpression of a number of other proteases has been reported to be associated with poor outcome in many cancers, such as urokinase plasminogen activator (37, 38), cathepsin D (39), and matrix metalloproteinase (40). In stage III-IV ovarian cancer, the tumor cells have already spread beyond the ovaries. hK10 may participate in a cascade reaction, which catalyzes the breakdown of extracellular barriers, and thus, overexpression of hK10 may facilitate ovarian tumor migration.

Early detection of ovarian cancer is hampered by the lack of a highly sensitive and specific biomarker. Currently, CA 125 is one widely-used serum marker for ovarian cancer, but it is not specific or sensitive enough for diagnosis (41-43). Other, newly introduced serum markers (44), such as inhibin (45, 46) and OVX1 (47) have shown some promise but have not gained wide acceptance. Serum hK6 (48) and serum hK10 concentration are significantly higher in ovarian cancer patients, compared to normal individuals. Overexpression of hK10 in ovarian tumors may account for its elevation in serum.

In summary, the study indicates that hK10 is an independent prognostic biomarker for late stage ovarian cancer.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

Below full citations are set out for the references referenced to in the specification.

TABLE 1

Analysis of hK10 in various biological fluids

| Biological Fluid | hK10 concentration (µg/L) | | | Number of samples tested | Positivity rate (%) |
| --- | --- | --- | --- | --- | --- |
| | Range | Mean (SD)[1] | Median | | |
| Breast milk | 0.1–32.3 | 6.8 (9.2) | 2.4 | 27 | 100 |
| Seminal plasma | 3.3–23.6 | 10.5 (5.8) | 8.9 | 24 | 100 |
| Amniotic fluid | 0.4–20.9 | 11.6 (5.6) | 11.9 | 23 | 100 |
| Male serum | 0.3–1.2 | 0.7 (0.2) | 0.7 | 29 | 100 |
| Female serum | 0.1–1.3 | 0.6 (0.3) | 0.6 | 28 | 100 |
| Cerebrospinal Fluid | 0.0–1.2 | 0.4 (0.3) | 0.3 | 19 | 95 |

[1]SD, standard deviation.

TABLE 2

Recovery of hK10 in various biological fluids.

| Sample | Initially present | Added hK10 (µg/L) | Recovered | Recovery (%) |
| --- | --- | --- | --- | --- |
| Serum 1 | 1.0 | 1.7 | 1.4 | 82 |
| | | 8.3 | 5.6 | 68 |
| Serum 2 | 0.3 | 1.7 | 1.4 | 82 |
| | | 8.3 | 5.6 | 68 |
| Serum 3 | 0.5 | 1.7 | 1.1 | 64 |
| | | 8.3 | 4.3 | 52 |
| CSF 1 | 0.5 | 1.7 | 1.5 | 88 |
| | | 8.3 | 7.9 | 95 |
| CSF 2 | 1.4 | 1.7 | 1.7 | 100 |
| | | 8.3 | 7.7 | 93 |
| Breast milk 1 | 2.0 | 1.7 | 1.3 | 77 |
| | | 8.3 | 5.2 | 63 |
| Breast milk 2 | 1.1 | 1.7 | 0.2 | 12 |
| | | 8.3 | 0 | 0 |
| Seminal plasma 1 | 3.2 | 1.7 | 1.6 | 96 |
| | | 8.3 | 7.3 | 87 |
| Seminal plasma 2 | 6.9 | 1.7 | 1.7 | 100 |
| | | 8.3 | 5.4 | 64 |
| Amniotic fluid 1 | 7.8 | 1.7 | 0.33 | 19 |
| | | 8.3 | 1.5 | 18 |
| Amniotic fluid 2 | 3.5 | 1.7 | 0.9 | 53 |
| | | 8.3 | 3.9 | 47 |

TABLE 3

Concentration of human kallikrein 10 (hK10) in serum of normal individuals and patients with various malignancies.

| Patient Group | Number of Samples | hK10 (µg/L) Min | hK10 (µg/L) Max | hK10 (µg/L) Median | hK10 (µg/L) 95$^{th}$ percentile | Number of patients with hK10 > 1.5 µg/L (%) | Number of patients with hK10 > 0.8 µg/L (%) |
|---|---|---|---|---|---|---|---|
| Normal males | 40 | 0 | 0.8 | 0.4 | 0.7 | 0 (0) | 0 (0) |
| Normal females | 42 | 0 | 0.8 | 0.3 | 0.7 | 0 (0) | 0 (0) |
| Breast cancer[1] | 22 | 0 | 1.1 | 0.6 | 1.0 | 0 (0) | 4 (18) |
| Medullary thyroid carcinoma[2] | 27 | 0 | 1.5 | 0.6 | 1.4 | 0 (0) | 7 (25.9) |
| Testicular cancer[3] | 51 | 0.1 | 1.1 | 0.6 | 2.5 | 1 (2) | 6 (11.8) |
| Gastrointestinal cancer[4] | 48 | 0.1 | 3.8 | 0.7 | 2.2 | 7 (14.6) | 22 (45.8) |
| Prostate cancer[5] | 41 | 0.2 | 1.5 | 0.5 | 1.3 | 0 (0) | 11 (26.8) |
| Lung cancer | 23 | 0.2 | 1.8 | 0.7 | 1.6 | 3 (13) | 7 (30.4) |
| Ovarian cancer[6] | 80 | 0.2 | 12.2 | 1.9 | 9.1 | 45 (56.2) | 62 (77.5) |

[1]With serum CA 15.3 levels ≥ 414 KU/L (upper ref. range 35 KU/L).
[2]With calcitonin levels ≥ 1,135 ng/L (upper ref. range 100 ng/L).
[3]With hCG levels ≥ 69 IU/L (upper ref. range 10 IU/L) or AFP levels ≥ 110 µg/L (upper ref. range 10 µg/L).
[4]With CA 19.9 levels ≥ 629 KU/L (upper ref. range 37 IU/L) and CEA levels ≥ 1,000 µg/L (upper ref. range 5 µg/L).
[5]With PSA levels ≥ 1,000 µg/L (upper ref. range 4 µg/L).
[6]With CA 125 levels ≥ 372 KU/L (upper ref. range 35 KU/L).

TABLE 4

Relationship between hK10 status and other variables in 182 ovarian cancer patients.

| Variable | Patients | hK10 low | hK10 high | P value |
|---|---|---|---|---|
| Stage | | | | |
| I | 42 | 21 (50.0) | 21 (50.0) | |
| II | 13 | 2 (15.4) | 11 (84.6) | 0.015[a] |
| III | 107 | 30 (28.0) | 77 (72.0) | |
| IV | 13 | 2 (15.4) | 11 (84.6) | |
| x[b] | 7 | | | |
| Grade | | | | |
| G1 | 21 | 10 (47.6) | 11 (52.4) | |
| G2 | 29 | 10 (34.5) | 19 (65.5) | 0.22[a] |
| G3 | 115 | 33 (28.7) | 82 (71.3) | |
| x | 17 | | | |
| Histotype | | | | |
| Serous | 81 | 12 (14.8) | 69 (85.2) | |
| Undifferentiated | 27 | 9 (33.3) | 18 (66.7) | |
| Endometrioid | 30 | 14 (46.7) | 16 (53.3) | |
| Mucinous | 11 | 4 (36.4) | 7 (63.6) | <0.001[c] |
| Clear cell | 13 | 8 (61.5) | 5 (38.5) | |
| Mullerian | 11 | 7 (63.6) | 4 (36.4) | |
| Others | 7 | 4 (57.1) | 2 (42.9) | |
| x | 2 | | | |
| Residual tumor (cm) | | | | |
| 0 | 76 | 32 (42.1) | 44 (57.9) | |
| 1-2 | 25 | 6 (24.0) | 19 (76.0) | 0.005[a] |
| >2 | 64 | 11 (17.2) | 53 (82.8) | |
| x | 17 | | | |
| Debulking success | | | | |
| OD[d] | 86 | 35 (40.7) | 51 (59.3) | 0.004[c] |
| SO[d] | 81 | 16 (19.8) | 65 (80.2) | |
| x | 15 | | | |
| Menopause | | | | |
| Pre/peri | 52 | 15 (28.8) | 37 (71.2) | 0.48[c] |
| Post | 130 | 46 (35.4) | 84 (64.6) | |
| Response to CTX[e] | | | | |
| NC/PD | 18 | 4 (22.2) | 14 (77.8) | 0.58[c] |
| CR/PR | 138 | 43 (31.2) | 95 (68.8) | |
| NE | 26 | | | |

[a]$\chi^2$ test.
[b]x, status unknown
[c]Fisher's Exact Test
[d]OD; Optimal debulking (0-1 cm),
SO; Suboptimal debulking (>1 cm)
[e]CTX; chemotherapy,
NC; no change,
PD; progressive disease,
CR; complete response,
PR; partial response,
NE; not evaluated.
x, status unknown

TABLE 5

Univariate and Multivariate Analysis of hK10 Expression with Progression-free and Overall Survival

| Variable | Progression-free survival | | | Overall survival | | |
|---|---|---|---|---|---|---|
| | HR[a] | 95% CI[b] | P value | HR[a] | 95% CI[b] | P value |
| Univariate analysis | | | | | | |
| hK10 | | | | | | |
| Low | 1.00 | | | 1.00 | | |
| High | 1.93 | 1.12–3.33 | 0.017 | 2.42 | 1.19–4.93 | 0.014 |
| As a continuous variable | 1.013 | 0.99–1.030 | 0.15 | 1.015 | 1.00–1.033 | 0.040 |
| Stage of disease (ordinal) | 2.82 | 2.07–3.84 | <0.001 | 3.33 | 2.22–5.0 | <0.001 |
| Grading (ordinal) | 2.20 | 1.59–3.03 | <0.001 | 2.33 | 1.53–3.55 | <0.001 |
| Residual tumor (ordinal) | 1.23 | 1.20–1.35 | <0.001 | 1.33 | 1.22–1.41 | <0.001 |
| Histologic type[c] | 0.68 | 0.46–1.01 | 0.059 | 0.74 | 0.46–1.21 | 0.23 |
| Age | 1.01 | 0.99–1.03 | 0.19 | 1.02 | 0.99–1.03 | 0.12 |
| Multivariate analysis | | | | | | |
| hK10 | | | | | | |
| Low | 1.00 | | | 1.00 | | |
| High | 1.15 | 0.64–2.06 | 0.62 | 1.21 | 0.58–2.50 | 0.60 |
| As a continuous variable | 1.02 | 0.99–1.04 | 0.11 | 1.02 | 0.99–1.04 | 0.19 |
| Stage of disease (ordinal) | 1.78 | 1.21–2.62 | 0.003 | 1.78 | 1.11–2.85 | 0.016 |
| Grading (ordinal) | 1.27 | 0.86–1.87 | 0.22 | 1.31 | 0.79–2.17 | 0.29 |
| Residual tumor (ordinal) | 1.17 | 1.08–1.26 | <0.001 | 1.22 | 1.11–1.34 | <0.001 |
| Histologic type[c] | 0.97 | 0.61–1.54 | 0.91 | 1.11 | 0.65–1.90 | 0.69 |
| Age | 1.01 | 0.99–1.04 | 0.14 | 1.01 | 0.98–1.04 | 0.23 |

[a]Hazards ratio (HR) estimated from Cox proportional hazards regression model
[b]Confidence interval of the estimated HR.
[c]Endometrial, undifferentiated and others vs. serous

TABLE 6

Cox proportional hazard regression analysis for subgroups of patients

| Variable | Progression-free survival | | | Overall survival | | |
|---|---|---|---|---|---|---|
| | HR[a] | 95% CI[b] | P | HR[a] | 95% CI[b] | P |
| Stage III/IV | | | | | | |
| HK10 unadjusted | 2.07 | 1.13–3.78 | 0.018 | 2.35 | 1.11–5.01 | 0.026 |
| HK10 adjusted[c] | 1.98 | 1.07–3.68 | 0.031 | 2.12 | 0.96–4.71 | 0.057 |
| Stage I–II | | | | | | |
| HK10 unadjusted | 0.69 | 0.14–3.28 | 0.64 | 1.73 | 0.17–16.9 | 0.63 |
| HK10 adjusted[c] | 1.14 | 0.23–5.46 | 0.86 | 2.43 | 0.24–24.7 | 0.45 |
| Tumor grade III | | | | | | |
| HK10 unadjusted | 1.91 | 0.93–3.16 | 0.083 | 2.26 | 1.01–5.08 | 0.047 |
| HK10 adjusted[d] | 0.94 | 0.48–1.81 | 0.85 | 1.09 | 0.48–2.45 | 0.83 |
| Tumor grade I–II | | | | | | |
| HK10 unadjusted | 3.85 | 1.12–13.2 | 0.031 | 3.58 | 0.80–16.1 | 0.094 |
| HK10 adjusted[d] | 2.01 | 0.52–7.68 | 0.32 | 2.58 | 0.52–12.8 | 0.24 |
| Suboptimal Debulking | | | | | | |
| HK10 unadjusted | 1.71 | 0.74–3.07 | 0.25 | 1.61 | 0.71–3.63 | 0.26 |
| HK10 adjusted[e] | 1.34 | 0.63–2.81 | 0.44 | 1.16 | 0.49–2.70 | 0.72 |
| Optimal Debulking | | | | | | |
| HK10 unadjusted | 0.74 | 0.25–2.17 | 0.59 | 1.36 | 0.25–7.48 | 0.71 |
| HK10 adjusted[e] | 0.72 | 0.22–2.28 | 0.58 | 1.26 | 0.20–7.78 | 0.79 |

[a]Hazards ratio (HR) estimated from Cox proportional hazards regression model
[b]Confidence interval of the estimated HR.
[c]Multivariate models were adjusted for tumor grade, residual tumor, histologic type and age
[d]Multivariate models were adjusted for stage of disease, residual tumor, histologic type and age.
[e]Multivariate models were adjusted for stage of disease, tumor grade, histologic type and age.

FULL CITATIONS FOR REFERENCES REFERRED TO IN THE SPECIFICATION

1. Bhoola K, Figueroa C and Worthy K Bioregulation of kinins: kallikreins, kininogens, and kininases. Pharmacol Rev 1992; 44:1-80. [Review].
2. Clements J A. The molecular biology of the kallikreins and their roles in inflammation. In: Farmer S G (ed) The Kinin System, Academic Press, 1997; 5, 71-97. [Review].
3. Riegman P H, Vlietstra R J, Suurmeijer L, Cleutjens C B and Trapman J. Characterization of the human kallikrein locus. Genomics 1992; 14:6-11.

4. McCormack R T, Rittenhouse H G, Finlay J A, Sokoloff R L, Wang T J, Wolfert R L, Lijia H and Oesterling J E. Molecular forms of prostate-specific antigen and the human kallikrein gene family a new era. Urology 1995; 45:729-44. [Review].
5. Rittenhouse H G, Finlay J A, Mikolajczyk S D and Partin A W. Human Kallikrein 2 (hK2) and prostate-specific antigen (PSA): two closely related, but distinct, kallikreins in the prostate. Crit Rev Clin Lab Sci 1998; 35:275-368. [Review].
6. Diamandis E P, Yousef G M, Luo L, Magklara I and Obiezu C V. The new human kallikrein gene family: Implications in carcinogenesis. Trends Endocrinol Metab 2000; 11:54-60. [Review].
7. Diamandis E P, Yousef G, Clements J, Ashworth L I Yoshida S, Egelrud T, Nelson P, Shiosaka S, Little S. Lilja H, Stenman U-H, Rittenhouse H and Wain H New nomenclature for the human tissue kallikrein gene family. Clin Chem (in press).
8. Liu X L, Wazer D E, Watanabe K and Band V. Identification of a novel serine protease-like gene, the expression of which is down-regulated during breast cancer progression. Cancer Res 1996; 56:3371-9.
9. Luo L Herbrick J A, Scherer S W, Beatty B, Squire J and Diamandis E P. Structural characterization and mapping of the normal epithelial cell-specific 1 gene. Biochem Biophys Res Commun 1998; 247:580-6.
10. Goyal J, Smith K M, Cowan J M, Wazer D E, Lee S W and Band V. The role for NES1 serine protease as a novel tumor suppressor. Cancer Res 1998; 58:4782-6.
11. Luo L Y, Grass L Howarth D J C, Thibault P, Ong H and Diamandis E P. Immunofluorometric assay of human kallikrein 10 (hK10; NES1) and its identification in biological fluids and tissues. Clin Chem [submitted].
12. Luo L Y and Diamandis E P. Down-regulation of the normal epithelial cell-specific 1 (NES1) gene is associated with unfavorable outcome in prostrate cancer. Clin Biochem 2000; 33:237. [Abstract].
13. Diamandis E P. Prostate sic antigen-its usefulness in clinical medicine. Trends Endocrinol Metab 1999; 25: 14-16.
14. McCormack R T, Rittenhouse H G, Finlay J A, Sokoloff R L, Wang T J, Wolfert R L, Lilja H and Oesterling J E. Molecular forms of prostate-specific antigen and the human kallikrein gene family: a new era Urology 1995; 45:729-44. [Review].
15. Chu T M. Prostate-specific antigen and early detection of prostate cancer. Tumor Biol 1997; 18:123-134.
16. Stenman U-H. New ultrasensitive assays facilitate studies on the role of human glandular kallikrein (hK2) as a marker for prostatic disease. Clin Chem 1999; 45:753-754.
17. Rittenhouse H G, Finlay J A, Mikolajczyk S D and Partin A W. Human Kallikrein 2 (hK2) and prostate-specific antigen (PSA): two closely related, but distinct, kallikreins in the prostate. Crit Rev Clin Lab Sci 1998; 35:275-368. [Review].
18. Christopoulos T K, Diamandis E P. Enzymatically amplified time-resolved fluorescence immunoassay with terbium chelates. Anal Chem 1992; 64:342-346.
19. Riman T, Persson I, Staffan N. Hormonal aspects of epithelial ovarian cancer: review of epidemiological evidence. Clin Endocrinol 1998; 49:695-707.
20. National Cancer Institute of Canada: Canadian Cancer Statistics 1999, Toronto, Canada, 1999.
21. Rosenthal A N, Jacobs I J, The role of CA 125 in screening for ovarian cancer. Int J Biol Markers 1998; 13:216-220.
22. Maggino T, Gadducci A. Serum markers as prognostic factors in epithelial ovarian cancer: an overview. Eur J Gynaecol Oncol 2000; 21:64-69.
23. Bast R C Jr, Xu F J, Yu Y H, Barnhill S, Zhang Z, Mills G B, CA 125: the past and the future. Int J Biol Markers 1998; 13:179-187.
24. Berek J S, Bast R C Jr. Ovarian cancer screening. The use of serial complementary tumor markers to improve sensitivity and specificity for early detection. Cancer 1995; 76:2092-2096.
25. Lambert-Messerlian G M. Is inhibin a serum marker for ovarian cancer? Eur J Endocrinol 2000; 42:331-333.
26. Burger H G, Baillie A, Drummond A E, healy D L, Jobling T, Mamers P, Robertson D M, et al. Inhibin and ovarian cancer. J Reprod Immunol 1998; 39:77-87.
27. Xu F J, Yu Y H, Daly L, DeSombre K, Anselmino L, Hass G M, Berchuck A, et al. OVX1 radioimmunoassay complements CA-125 for predicting presence of residual ovarian carcinoma at second-look surgical surveillance procedures. J Clin Oncol 1993; 11:1506-1510.
28. Cox, D. R. J. R. Stat. Soc., 34: 187-202, 1972.
29. Kaplan, E. L. and Meier, P. Nonparametric estimation from incomplete observations. J. Am. Stat. Assoc., 53: 457-481, 1958.
30. Mantel, N. Cancer Chemother. Rep. 50:163-170, 1966.
31. Pisani, P., Parkin, D. M., and Ferlay, J. Estimates of the worldwide incidence of eighteen major cancers in 1985. Implications for prevention and projections of future burden. Int. J. Cancer, 55: 891-903, 1993.
32. Ozols, R F., Schwartz, P. E., and Eifel, P. J. Ovarian cancer, fallopian tube carcinoma and peritoneal carcinoma. In: V. T. Devita, S. Hellman, and S. A Rosenberg (eds.), Cancer: principles and practice of oncology, 3 edition, Vol. 2, pp. 1502-1534. Philadelphia: Lippincott, 1994.
33. Piver, M. S. Ovarian carcinoma: a decade of progression Cancer, 54: 2706-2715, 1994.
34. Trope, C. Prognostic factors in ovarian cancer. Cancer Treat. Res., 95: 287-352, 1998.
35. Aznavoorian, S., Murphy, A. N., Stetler-Stevenson, W. G., and Liotta, L. Molecular aspects of tumor cell invasion and metastasis. Cancer, 71: 1368-1383, 1993.
36. Duffy, M. J. Role of proteolytic enzymes in cancer invasion and metastasis. Clin. & Exp. Metastasis, 10: 145-155, 1992.
37. Duff, M. J., Reilly, D., O'Sullivan, C., O'Higgins, N., Fennelly, J. J., and Andreasen, P. Urokinase plasminogen activator, a new and independent prognostic marker in breast cancer. Cancer Res., 50: 6827-6829, 1990.
38. Foekens, J. S., Schmitt, M., Pache, L., Van Putton, W., Peters, H. A., Bontenbal, A, Janicke, F., and Klijin, J. G. M. Prognostic value of urokinase-type plasminogen activator in 617 primary breast cancer patients. Cancer Res., 52: 6101-6105, 1992.
39. Thorpe, S., Rochefort, H., Garcia, M., Freiss, G., Christensen, I. J., Khalaf, S., Paulucci, F., Pau, P., Rasmussen, B. B., and Rose, C. Association between high concentrations of Mr 52,000 cathepsin D and poor prognosis in primary human breast cancer. Cancer Res., 49: 6008-6014, 1989.
40. Daidone, M. G., Silvestrini, R. D'Errico, A., Di Fronzo, G., Benini, E., Mancini, A. M., Garbisa, S., Liotta, L. A., and Grigioni, W. F. Laminin receptors, collagenase IV and prognosis in node-negative breast cancer. Int. J. Cancer, 48: 529-532, 1991.
41. Rosenthal, A. N., Jacobs, I. J. The role of CA 125 in screening for ovarian cancer. Int. J. Biol. Markers, 1998; 13:216-220.
42. Maggino, T., Gadducci, A. Serum markers as prognostic factors in epithelial ovarian cancer: an overview. Eur. J. Gynaecol. Oncol., 2000; 21:64-69.

43. Bast, R. C. Jr., Xu, F. J., Yu, Y. H., Barnhill, S., Zhang, Z., Mills, G. B. CA 125: the past and the future. Int J. Biol. Markers, 1998; 13:179-187.
44. Berek, J. S., Bast, R. C. Jr. Ovarian cancer screening. The use of serial complementary tumor markers to improve sensitivity and specificity for early detection. Cancer, 1995; 76:2092-2096.
45. Lambert-Messerlian, G. M. Is inhibin a sere marker for ovarian cancer? Eur. J. Endocrinol., 2000; 42:331-333.
46. Burger, H. G., Baillie, A., Drummond, A. E., Healy, D. L., Jobling, T., Mamers, P, Robertson, D. M., et al. Inhibin and ovarian cancer. J. Reprod. Immunol., 1998; 39:77-87.
47. Xu, F. J., Yu, Y. H., Daly, L., DeSombre, K., Anselmino, L., Hass, G. M., Berchuck, A., et al. OVX1 radioimmunoassay complements CA-125 for predicting presence of residual ovarian carcinoma at second-look surgical surveillance procedures. J. Clin. Oncol., 1993; 11:1506-1510.
48. Luo, L. Y., Bunting, P., Scorilas, A., and Diamandis, E. P. Human kallikrein 10: A novel tumor-marker for ovarian carcinoma? Clin. Acta, 2001; 306:111-118

We claim:

1. A method of evaluating the probability of the presence of ovarian cancer in a subject, the method comprising:
   measuring the amounts of human kallikrein 10 (hK10) in a biological sample from the subject;
   comparing the measured amounts of hK10 in the biological sample to an hK10 standard, wherein said hK10 standard is a level of hK10 obtained from a sample of a member of the group consisting of a healthy subject, a subject with normal or benign ovarian tissue, and a subject having early stage ovarian cancer, and
   identifying an increase in the amount of hK10 in the biological sample as compared to the hK10 standard, wherein said increase is indicative of the probability of the presence of malignant or pre-malignant cells of ovarian cancer.

2. The method as claimed in claim 1, wherein said measuring comprises contacting the biological sample with an antibody specific for hK10 which is directly or indirectly labeled

SEQUENCE LISTING

<160> NUMBER OF SEQ ID NOS: 4

<210> SEQ ID NO 1
<211> LENGTH: 28
<212> TYPE: DNA
<213> ORGANISM: Artificial Sequence
<220> FEATURE:
<223> OTHER INFORMATION: Primer

<400> SEQUENCE: 1
aacgacgaat tcttggaccc cgaagcct                                28

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
cgtagaattc ggatcagttg ga                                     22

<210> SEQ ID NO 3
<211> LENGTH: 15
<212> TYPE: PRT
<213> ORGANISM: Homo sapiens

<400> SEQUENCE: 3

Val Gly Asp Asp His Leu Leu Leu Leu Gln Gly Glu Gln Leu Arg
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: Fragment Ions

<400> SEQUENCE: 4

Gly Gln Leu Leu Leu Leu His
1               5 with a detectable substance and determining the amount of hK10 by measuring the detectable substance.

3. The method as claimed in claim 1, wherein said measuring comprises incubating the sample with a first antibody specific for hK10 which is directly or indirectly labeled with a detectable substance and a second antibody specific for hK10 which is immobilized; separating and removing unbound first antibody from the second antibody; and determining the amount of hK10 by measuring the detectable substance.

4. The method as claimed in claim 3, wherein the first and second antibodies are contacted simultaneously or sequentially with the biological sample.

5. The method as claimed in claim 2 or 3, wherein the detectable substance is alkaline phosphatase.

6. The method as claimed in claim 5, wherein the alkaline phosphatase is detected using a fluorogenic substrate.

7. The method as claimed in claim 2 or 3, wherein each antibody is independently selected from the group consisting of a monoclonal antibody, a polyclonal antibody, immunologically active antibody fragment, humanized antibody, an antibody heavy chain, an antibody light chain, a genetically engineered single chain Fv molecule, or a chimeric antibody.

8. The method as claimed in claim 1, wherein hK10 is measured using time-resolved fluorescence.

9. The method according to claim 1, further comprising identifying an increase of greater than 1.5 µg/L hK10 in the amount of hK10 in the biological sample as compared to the hK10 standard.

10. The method according to claim 1, wherein the sample is selected from the group consisting of serum, tumor tissue extract, and cytosolic extract derived from the subject.

11. The method according to claim 1, further comprising measuring the amount of an additional biomarker in said sample.

12. The method according to claim 11, wherein said additional biomarker is selected from the group consisting of human stratum corneum chymotryptic enzyme, human kallikrein 4 (hK4), human kallikrein 5 (hK5), human kallikrein 6 (hK6), human kallikrein 8 (hK8), human kallikrein 9 (hK9), CA125, CA15-3, CA19-9, OVX1, lysophosphatidic acid, and carcinoembryonic antigen.

13. The method according to claim 12, wherein the additional marker is CA125.

14. The method according to claim 13, wherein the amount of CA125 is greater than 35 KU/L.

15. The method according to claim 12, wherein the additional markers are hK6 and CA125.

16. The method according to claim 1, wherein the ovarian cancer is late stage ovarian cancer.

17. A method of evaluating the probability of the presence of ovarian cancer in a subject, the method comprising:
measuring the amounts of human kallikrein 10 (hK10) and at least one additional marker in a biological sample from the subject;
comparing the measured amounts of hK10 and said additional marker in the biological sample to an hK10 standard and additional marker standard, respectively, wherein said hK10 standard and additional marker standards are levels of hK10 and the additional marker, respectively, obtained from a sample of a member of the group consisting of a healthy subject, a subject with normal or benign ovarian tissue, and a subject having early stage ovarian cancer, and
identifying an increase in the amount of hK10 in the biological sample as compared to the hK10 standard coupled with a change in the amount of the additional marker in the biological sample as compared to the additional marker standard, wherein said increase is indicative of the probability of the presence of malignant or pre-malignant cells of ovarian cancer.

* * * * *